(12) United States Patent
Yi et al.

(10) Patent No.: US 8,567,072 B2
(45) Date of Patent: Oct. 29, 2013

(54) SAFETY SCALPEL

(75) Inventors: Patrick Yi, Montery Park, CA (US);
George Hatzilias, Buford, GA (US)

(73) Assignee: Medipurpose PTE Ltd, Singapore (SG)

( * ) Notice: Subject to any disclaimer, the term of this patent is extended or adjusted under 35 U.S.C. 154(b) by 0 days.

(21) Appl. No.: 13/701,510

(22) PCT Filed: Jun. 28, 2011

(86) PCT No.: PCT/SG2011/000228
§ 371 (c)(1),
(2), (4) Date: Feb. 27, 2013

(87) PCT Pub. No.: WO2012/002910
PCT Pub. Date: Jan. 5, 2012

(65) Prior Publication Data
US 2013/0158574 A1    Jun. 20, 2013

Related U.S. Application Data

(60) Provisional application No. 61/359,249, filed on Jun. 28, 2010.

(51) Int. Cl.
*A61B 17/32*  (2006.01)
(52) U.S. Cl.
USPC .............. 30/162; 30/335; 30/339; 606/167
(58) Field of Classification Search
USPC ............. 30/162, 335, 339; 606/167, 170
See application file for complete search history.

(56) References Cited

U.S. PATENT DOCUMENTS

| | | | |
|---|---|---|---|
| 5,299,357 A | 4/1994 | Wonderley | |
| 5,330,493 A * | 7/1994 | Haining | 606/167 |
| 5,342,379 A | 8/1994 | Volinsky | |
| 5,571,127 A * | 11/1996 | DeCampli | 606/167 |
| 5,741,289 A * | 4/1998 | Jolly et al. | 606/181 |
| 5,908,432 A * | 6/1999 | Pan | 606/167 |
| 5,924,206 A * | 7/1999 | Cote et al. | 30/337 |
| 5,941,892 A * | 8/1999 | Cohn et al. | 606/167 |
| 6,022,364 A * | 2/2000 | Flumene et al. | 606/166 |
| 6,053,929 A * | 4/2000 | Cohn et al. | 606/167 |
| 6,254,621 B1 * | 7/2001 | Shackelford et al. | 606/167 |
| 6,589,258 B2 * | 7/2003 | Pilo et al. | 606/167 |
| 6,757,977 B2 * | 7/2004 | Dambal et al. | 30/162 |
| 6,884,240 B1 * | 4/2005 | Dykes | 606/1 |

(Continued)

OTHER PUBLICATIONS

International Search Report mailed Sep. 19, 2011 for priority application PCT/SG2011/000228.

(Continued)

*Primary Examiner* — Hwei C Payer
(74) *Attorney, Agent, or Firm* — Ryan A. Schneider, Esq.; Troutman Sanders LLP

(57) ABSTRACT

A safety scalpel incorporating a handle similar in thickness, length, weight, balance, shape and feel to the conventional metal handle preferred by most surgeons, and a disposable cartridge assembly that is easily mounted and released from the scalpel handle. The handle comprises a first end and a second end. The cartridge assembly comprises a blade guard/shield that can be slideably mounted onto the second end of the handle, a blade holder/slider that can be disposed within the blade guard, and a blade that can be attached to the blade holder. The safety scalpel incorporates a locking system that prevents the cartridge assembly from sliding off or wobbling on the handle during use.

26 Claims, 25 Drawing Sheets

(56) References Cited

U.S. PATENT DOCUMENTS

| | | | |
|---|---|---|---|
| 7,101,382 B2 * | 9/2006 | George et al. | 606/167 |
| 7,159,713 B1 * | 1/2007 | Austria | 206/355 |
| 7,172,611 B2 * | 2/2007 | Harding et al. | 606/167 |
| 7,207,999 B2 * | 4/2007 | Griffin et al. | 606/167 |
| 7,669,337 B2 * | 3/2010 | Yi et al. | 30/155 |
| 8,015,712 B2 * | 9/2011 | Yi et al. | 30/162 |
| 8,181,352 B1 * | 5/2012 | Shackelford et al. | 30/162 |
| 8,205,340 B2 * | 6/2012 | Austria et al. | 30/162 |
| 8,464,430 B2 * | 6/2013 | Cote | 30/162 |
| 2006/0095057 A1 * | 5/2006 | Yi et al. | 606/167 |
| 2006/0100650 A1 | 5/2006 | Kiehne | |
| 2006/0241664 A1 | 10/2006 | Lam | |
| 2007/0255298 A1 | 11/2007 | Djordjevic | |
| 2007/0265651 A1 | 11/2007 | Yi | |
| 2009/0165310 A1 * | 7/2009 | Nakamura | 30/335 |
| 2012/0245610 A1 * | 9/2012 | Hajgato et al. | 606/167 |

OTHER PUBLICATIONS

International Preliminary Report on Patentability completed May 15, 2012.

\* cited by examiner

SAFETY SCALPEL

CROSS-REFERENCE TO RELATED APPLICATION

This Application claims priority to U.S. Provisional Patent Application No. 61/359,249, entitled "Safety Scalpel," filed 28 Jun. 2010, which is hereby incorporated herein as if fully set forth below.

BACKGROUND

1. Technical Field

Embodiments of the present invention relate to cutting devices and, more particularly, to safety scalpels for medical use.

2. Description of Related Art

Health care is the second fastest growing sector of the U.S. economy, employing over 12 million workers. Health care workers face a wide range of hazards on the job—including needlestick and sharps injuries, back injuries, latex allergies, violence, and stress. Although it is possible to prevent or reduce health care worker exposure to these hazards, health care workers are actually experiencing increasing numbers of occupational injuries and illnesses. Rates of occupational injury to health care workers continue to rise; as they have over the past decade. By contrast, two of the most hazardous industries, agriculture and construction, are safer today than they were a decade ago.

Precise national data is not available on the annual number of needlestick and other percutaneous injuries among health care workers; however, estimates indicate that 600,000 to 800,000 such injuries occur annually. About half of these injuries go unreported. Data from EPINet (the Exposure Prevention Information Network) suggests that at an average hospital, workers incur approximately thirty needlestick injuries per 100 beds per year.

Most reported needlestick and sharps injuries involve nursing staff, but laboratory staff, physicians, housekeepers, and other health care workers are also injured. Some of these injuries expose workers to bloodborne pathogens that can cause infection. The more serious of these pathogens are the hepatitis B virus (HBV), the hepatitis C virus (HCV), and the human immunodeficiency virus (HIV). Infections by each of these pathogens are potentially life threatening, yet preventable.

The emotional impact of needlestick and sharps injuries can be severe and long lasting, even when a serious infection is not transmitted. This impact is particularly severe when the injury involves exposure to HIV. In one study of twenty health care workers with an HIV exposure, eleven reported acute severe distress, seven had persistent moderate distress, and six quit their jobs as a result of the exposure. Other stress reactions requiring counseling have also been reported. Not knowing the infection status of the source patient can accentuate the health care worker's stress. In addition to the exposed health care worker, colleagues and family members may suffer emotionally.

Safety and health issues can best be addressed in the setting of a comprehensive prevention program that considers all aspects of the work environment and that has employee involvement as well as management commitment. Implementing the use of improved engineering controls is one component of such a comprehensive program. Other prevention strategy factors that must be addressed, however, include modification of hazardous work practices, administrative changes to address needle hazards in the environment (e.g., prompt removal of filled sharps disposal boxes), safety education and awareness, feedback on safety improvements, and action taken on continuing problems.

Improved engineering controls are often among the most effective approaches to reducing occupational hazards and, therefore, are an important element of a needlestick prevention program. Such controls include eliminating the unnecessary use of needles and implementing devices having safety features. A number of sources have identified several desirable characteristics for safety devices, which include preferences for safety devices that: do not use needles; incorporate the safety feature as an integral part of the device; work passively (i.e., requires no activation by the user); have a safety feature that can be engaged with a single-hand technique and allows the worker's hands to remain behind the exposed sharp, if user activation is necessary; allow the user to easily determine whether the safety feature is activated; have a safety feature that cannot be deactivated and remains protective through disposal; perform reliably; are easy to use and practical; and are safe and effective for patient care.

Although each of these characteristics is desirable, some are not feasible, applicable, or available for certain health care situations. For example, needles will always be necessary where alternatives for skin penetration are not available. Also, a safety feature that requires activation by the user might be preferable to one that is passive in some cases. Each device must be considered on its own merit and ultimately on its ability to reduce workplace injuries.

Regarding specifically scalpels, the conventional scalpel currently used in the healthcare industry includes a metal handle and a disposable blade that is mounted on the handle prior to use, and removed after use. The process of mounting and dismounting the blade is a difficult and dangerous procedure, which exposes the medical practitioner to potential injury from the exposed blade and contamination due to blood that may be present on the blade.

An additional danger exists during operations. When a surgeon requests a particular scalpel, a nurse, physician's assistant, or scrub technician must hand the scalpel to the surgeon with the handle end pointed toward the surgeon, so the surgeon can easily grasp the scalpel. Consequently, the nurse must hold the scalpel by the end having an exposed blade. As a result, the nurse is often cut by the blade during the hand off. Similarly, when the surgeon returns the scalpel to the nurse, the surgeon presents the nurse with the blade end, which the nurse must grab without cutting herself/himself.

Surgeons who have developed a feel for the shape and weight of the metal handle dislike the current disposable safety scalpels as, among other things, the plastic handle is too light and feels "different." During use, the plastic handle of the scalpel incurs more undesirable flexibility than that of a metal handle scalpel. In addition, the disposable safety scalpel is significantly more expensive than the regular disposable blade. These two factors currently limit the adoption of safety scalpels in the healthcare industry.

What is needed is a safe and reliable scalpel that overcomes the present objections from the healthcare practitioner of current designs, while providing adequate protection for the medical workers handling the scalpel.

SUMMARY

Briefly described, embodiments of the present invention relate to a safety scalpel. The safety scalpel is an improvement over the conventional scalpel by providing a safety scalpel that incorporates a handle similar in thickness, length, weight, balance, shape and feel to the conventional metal handle preferred by most surgeons, and a cartridge assembly that is easily mounted and released from the scalpel handle. The handle can be reusable and made of a metal. The cartridge assembly can be made of disposable materials and thus can be preferably detachable from the handle. The cartridge assembly comprises a shield, a slider carrying a blade, and a button to move the blade between engaging and disengaging positions. For example, the blade extends from the housing during use and is fully housed in the housing when the scalpel is not being used.

In an exemplary embodiment, the safety scalpel can comprise a handle having a first end and a second end, a cartridge assembly comprising a shield fitting onto the second end of the handle, a slider disposed within the shield, and a blade attached to the slider.

The second end of the handle can be generally flat and narrower than the first end of the handle. The shield can be generally elongate, generally rectangular in cross-section, and substantially hollow. The second end of the handle can be inserted into the shield and secured thereto to define a cavity. A locking snap incorporated into the shield can engage a defined aperture of the handle to lock the cartridge onto the handle.

In some embodiments, when the cartridge assembly is fully assembled the blade housed therein cannot be extended unless it is placed on the handle. This feature prevents accidental extension of the blade and reduces injuries.

In some embodiments, the safety scalpel is configured to extend/retract. For example, this familiar/intuitive action is similar to using a conventional box cutter device. As opposed to some of the conventional scalpels, where the user must slide the shield backwards to expose the blade and even more awkwardly slide the shield forward to consciously cover the blade, the present safety scalpel is adapted to extend and retract by pushing downward on the button and then sliding along the shield to change its position.

Further features of embodiments of the present invention, and the advantages offered thereby, are explained in greater detail hereinafter with reference to specific embodiments illustrated in the accompanying drawings, wherein like elements are indicated by like reference designators.

DETAILED DESCRIPTION

Figure 1:
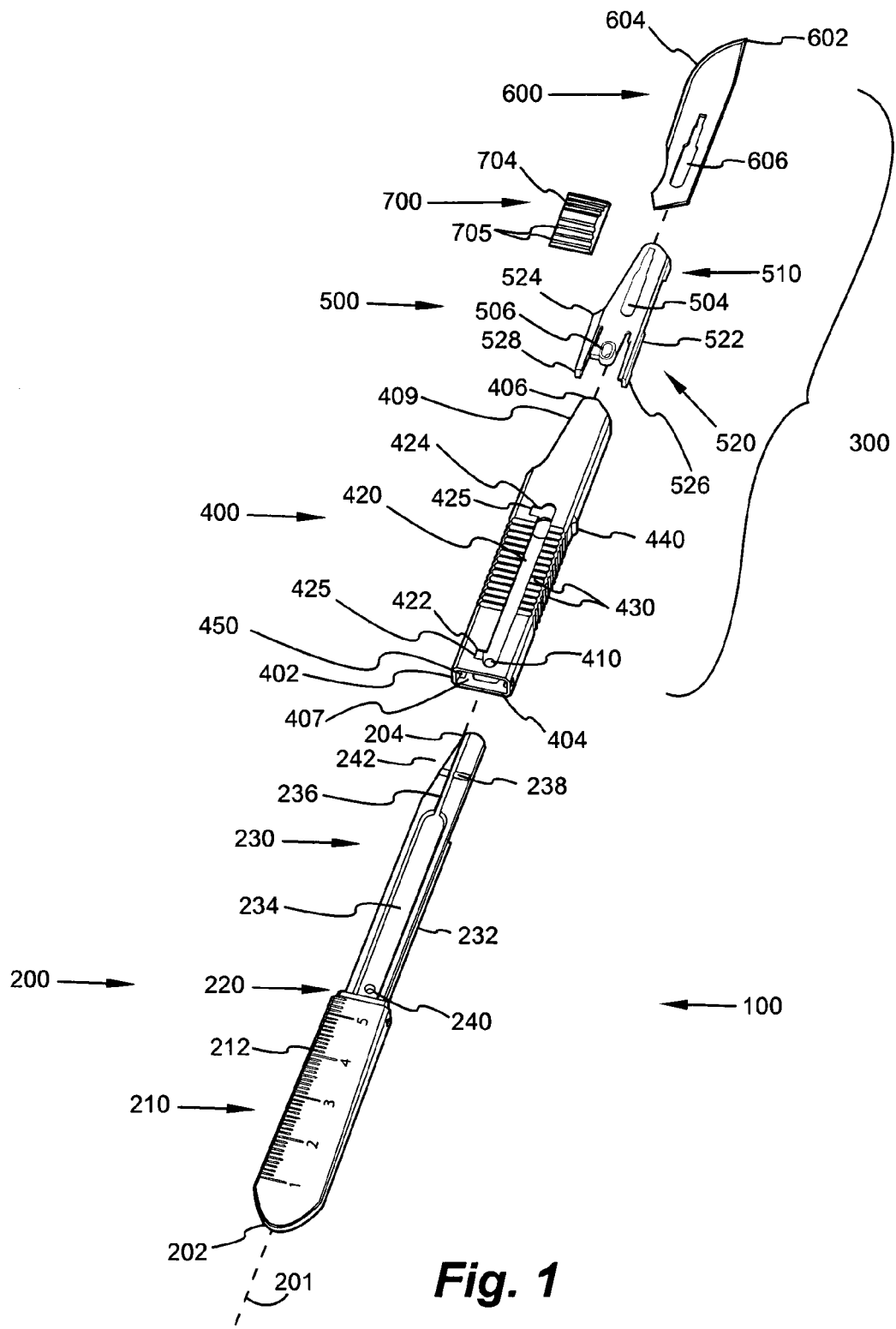
FIG. 1 is an exploded assembly view of a safety scalpel, in accordance with an exemplary embodiment of the present invention.

Although preferred embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Referring now in detail to the figures, wherein like reference numerals represent like parts throughout the several views, FIG. 1 illustrates an exploded assembly view of an exemplary embodiment of a safety scalpel 100. The safety scalpel 100 can have a longitudinal axis 201 and comprise a handle 200 and a cartridge assembly 300. The cartridge assembly 300, which in many embodiments may be disposable, can be detachably mounted on the handle 200. Preferably, the cartridge assembly 300 can be mounted on the handle 200 by sliding the cartridge assembly 300 substantially parallel to the longitudinal axis 201. The handle 200 can have a wall or a stopping surface for limiting how, far the cartridge assembly 300 can slide onto the handle 200.

Figure 8A:
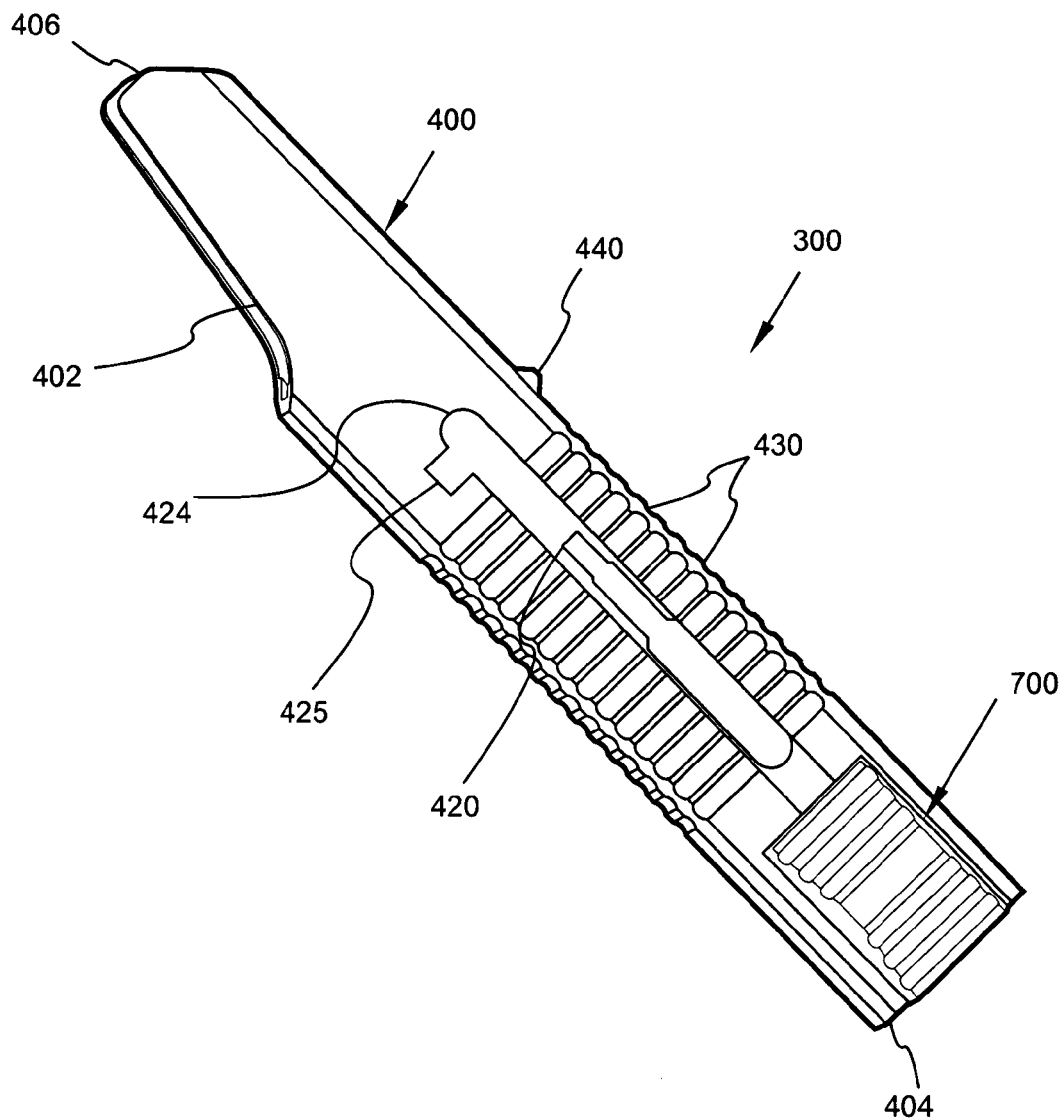
FIG. 8A is a front, perspective view of the cartridge assembly of the safety scalpel, in accordance with an exemplary embodiment of the present invention.

As shown in the figures, in particular, FIGS. 1 and 8A, the cartridge assembly 300 includes a shield 400, which may also be referred to as a blade guard, a guard, or housing; a slider 500, which may also be referred to as a blade holder, a blade 600; and an activation member 700, which may also be referred to as a button.

Figure 2:
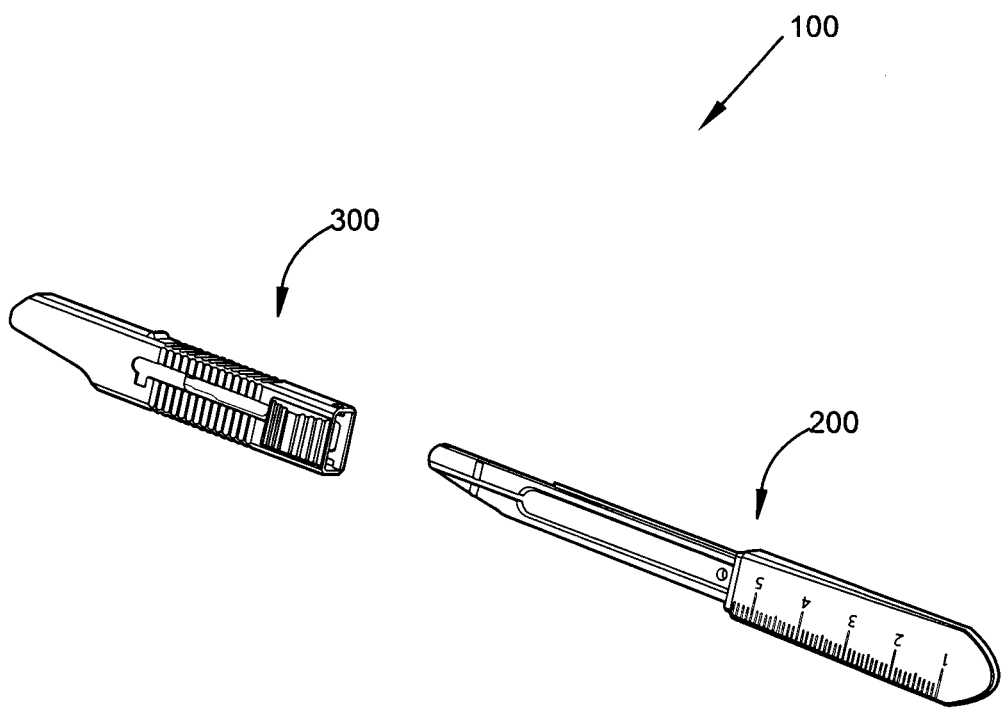
FIG. 2 is a front, perspective view of a handle and a cartridge assembly of the safety scalpel, in accordance with an exemplary embodiment of the present invention.

FIG. 2 illustrates a front, perspective view of the handle 200 and the cartridge assembly 300 before assembly of the safety scalpel 100.

Figure 3:
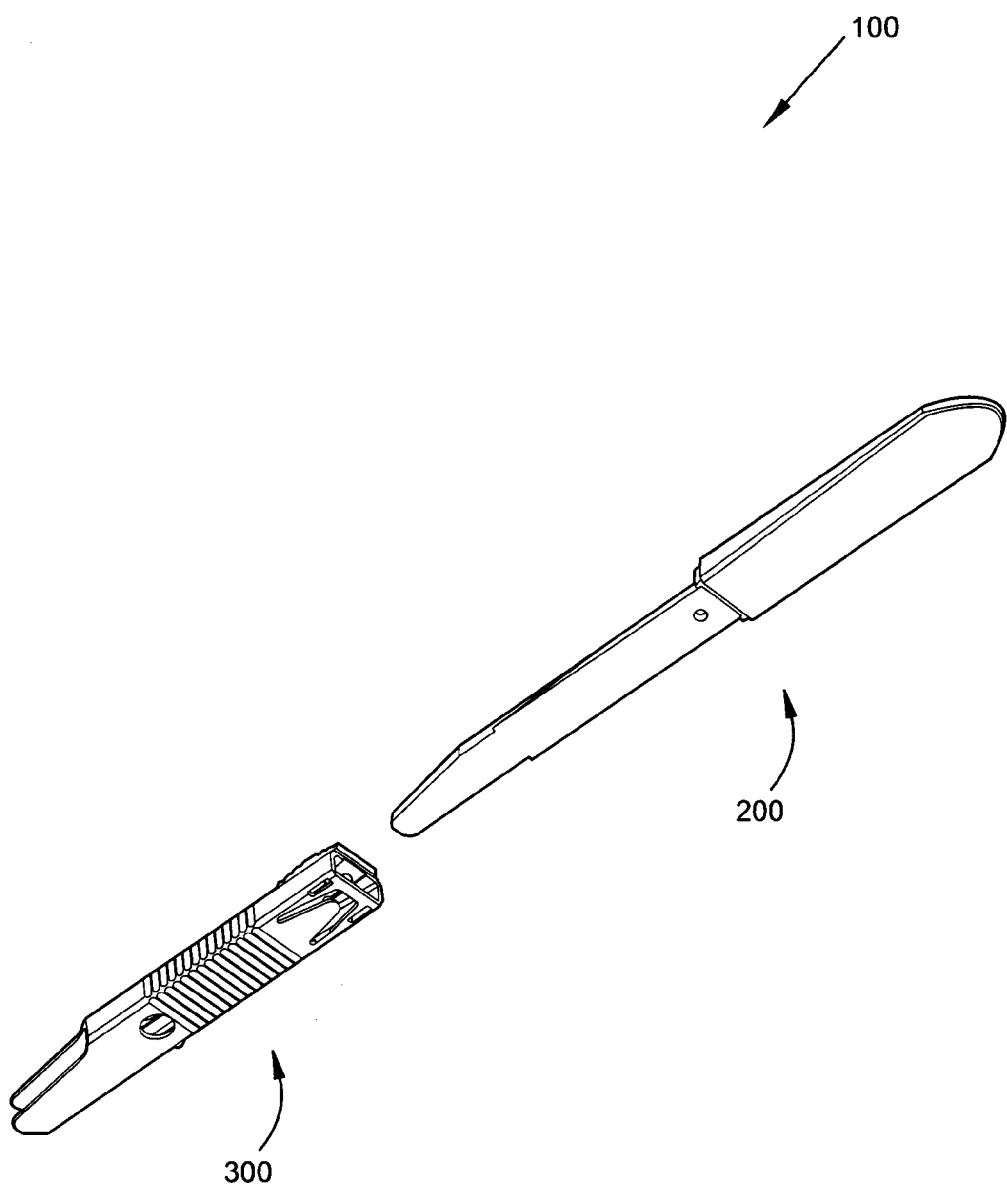
FIG. 3 is a rear, perspective view of the handle and the cartridge assembly of the safety scalpel, in accordance with an exemplary embodiment of the present invention.

FIG. 3 is a rear, perspective view of the handle 200 and the cartridge assembly 300 before assembly of the safety scalpel 100.

Figure 4:
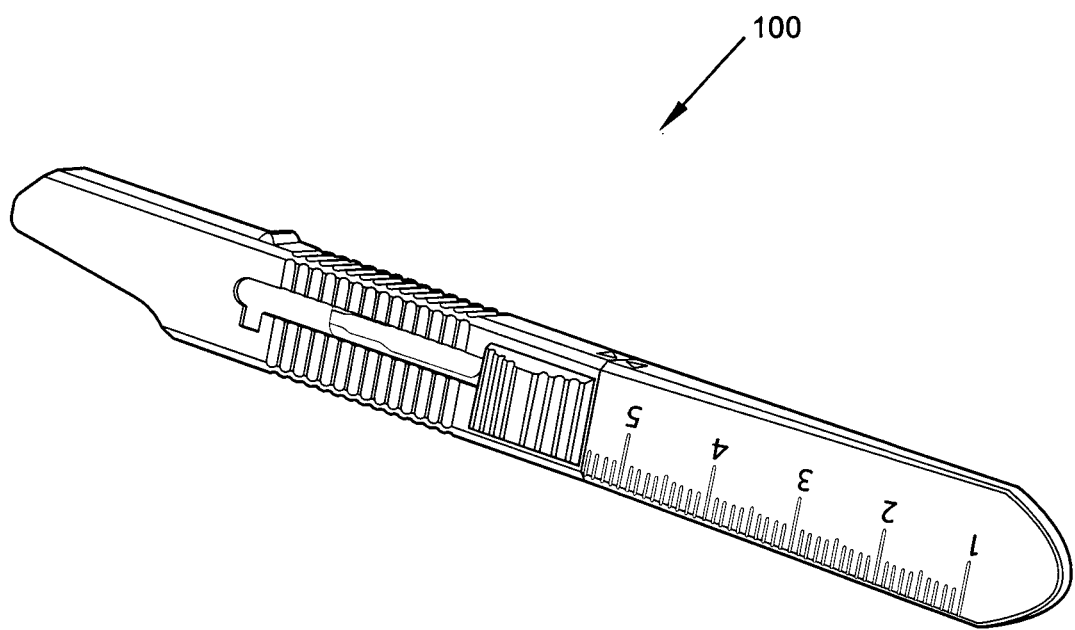
FIG. 4 is a front, perspective view of the safety scalpel with a blade in a retracted position, in accordance with an exemplary embodiment of the present invention.
Figure 5:
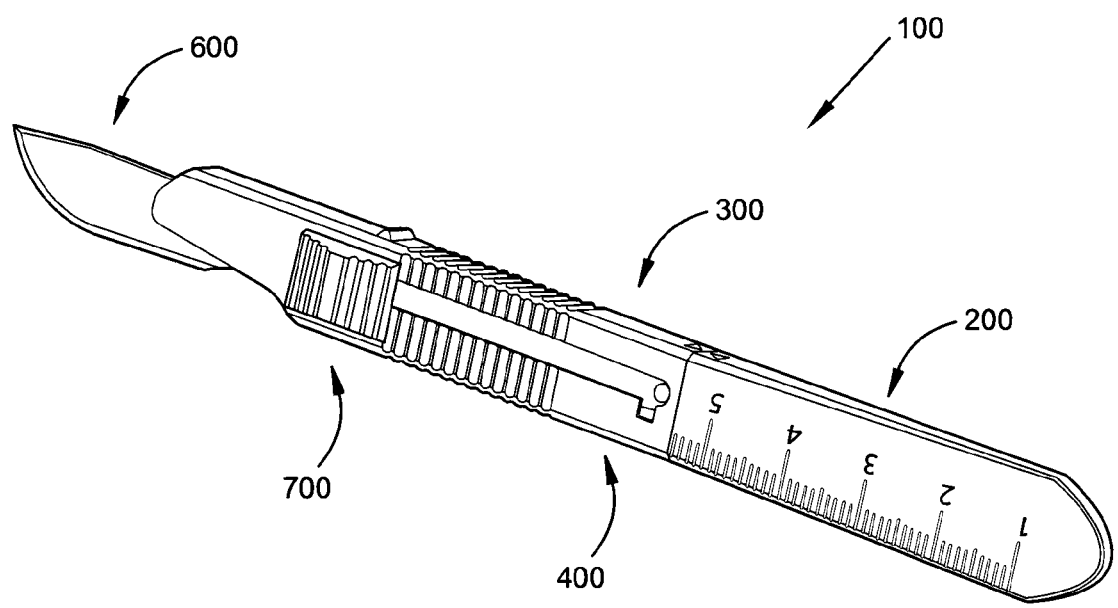
FIG. 5 is a front, perspective view of the safety scalpel with a blade in an extended position, in accordance with an exemplary embodiment of the present invention.
Figure 6:
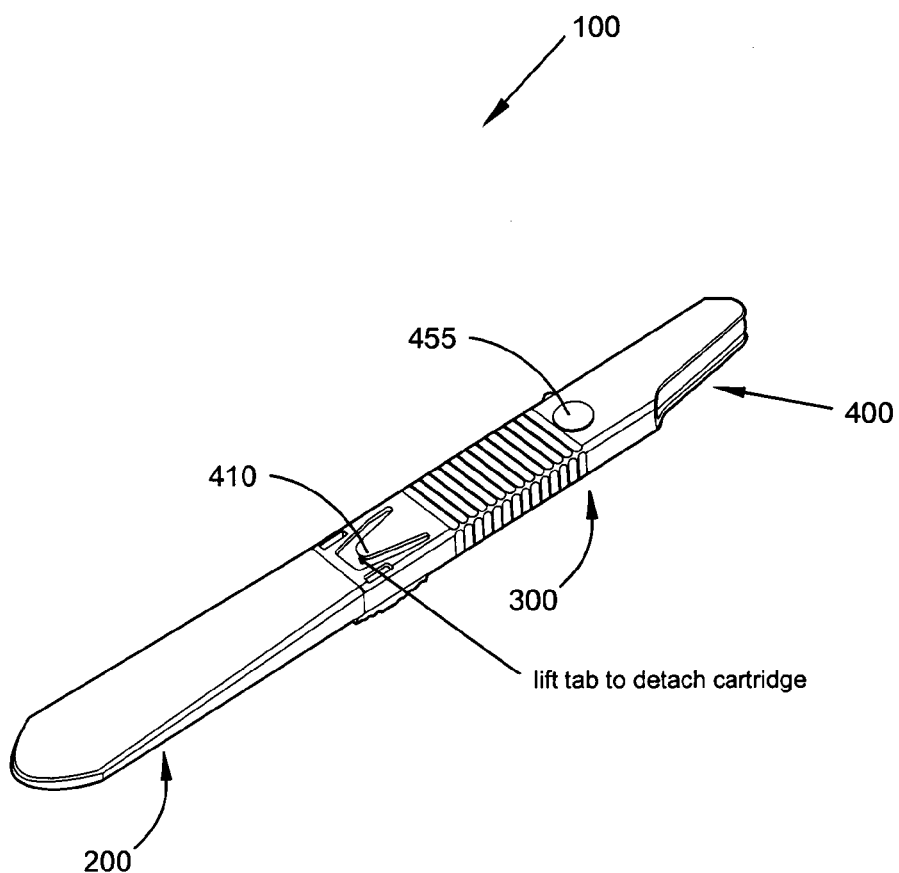
FIG. 6 is a rear, perspective view of the assembled safety scalpel with a blade in a refracted position, in accordance with an exemplary embodiment of the present invention.
Figure 7A:
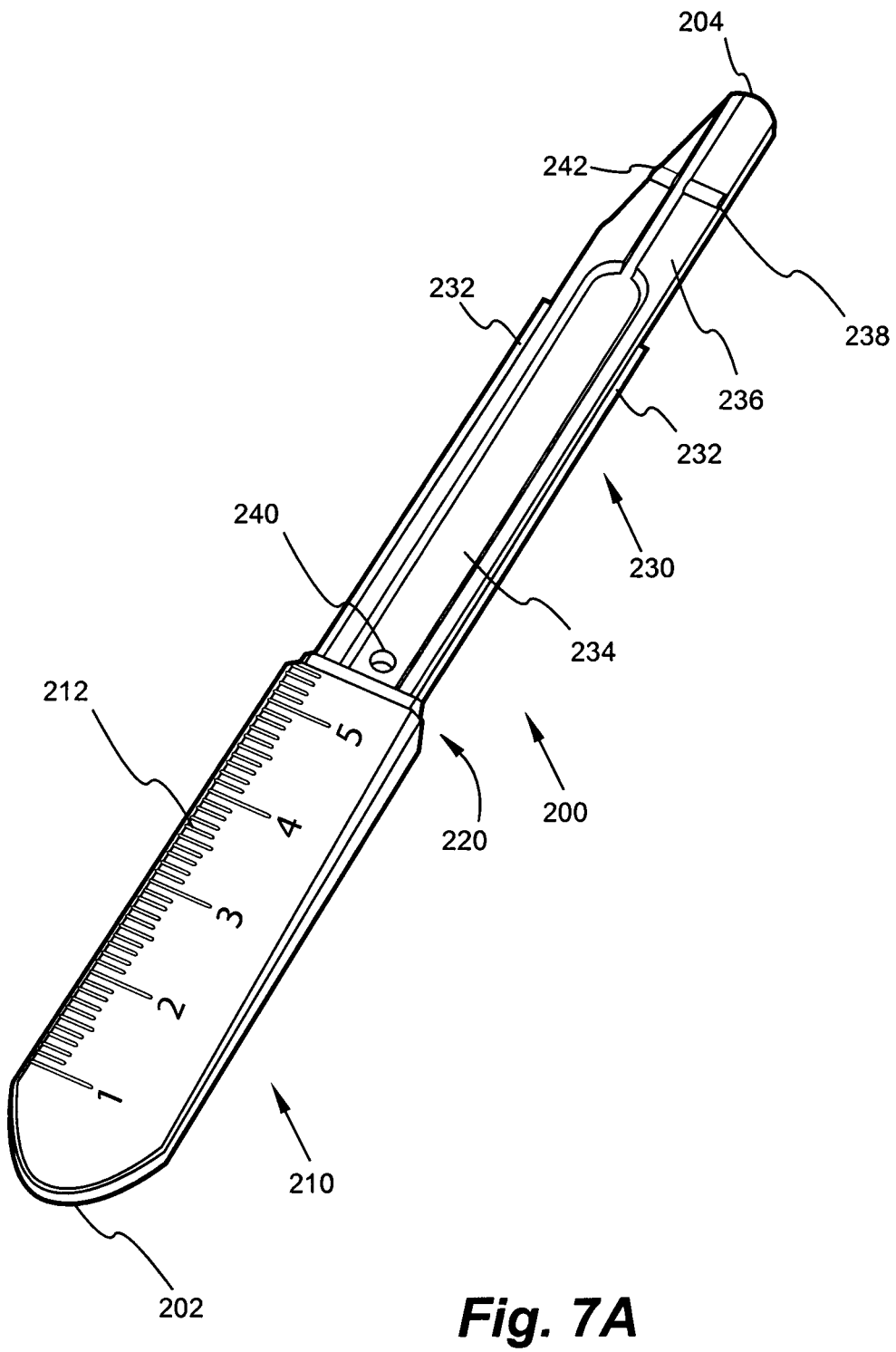
FIG. 7A is a front view of the handle of the safety scalpel, in accordance with an exemplary embodiment of the present invention.
Figure 7B:
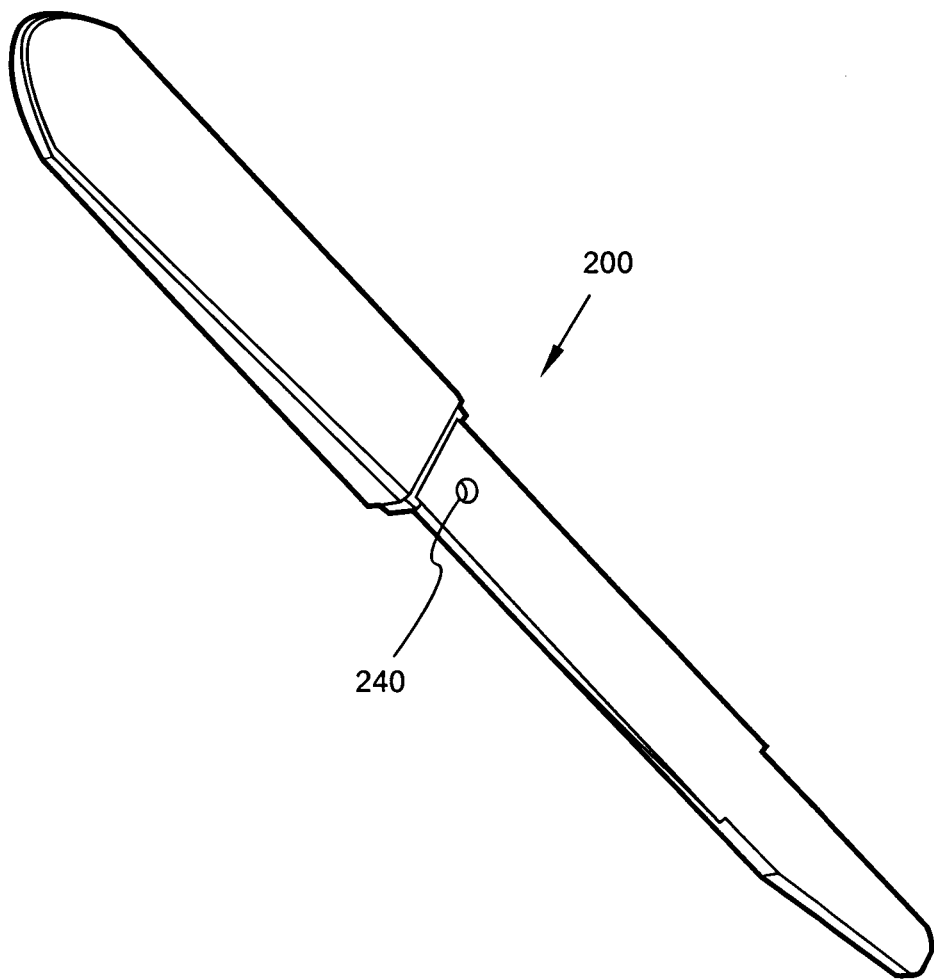
FIG. 7B is a rear view of the handle of the safety scalpel, in accordance with an exemplary embodiment of the present invention.
Figure 7C:
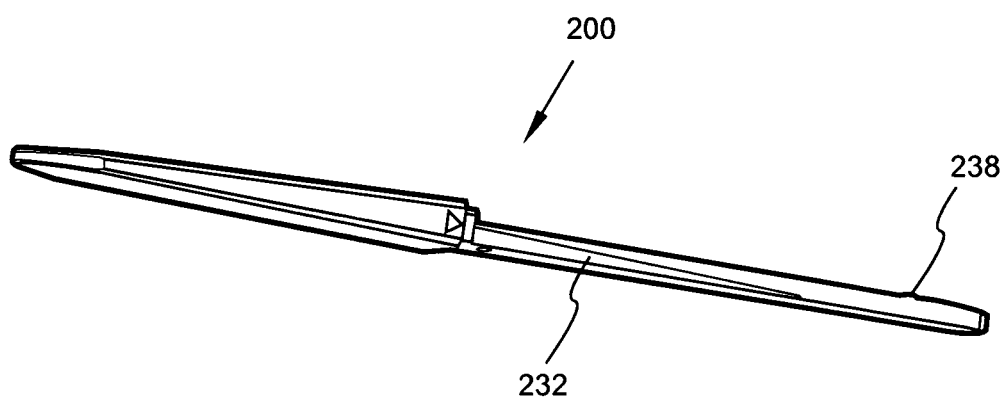
FIG. 7C is a side view of the handle of the safety scalpel, in accordance with an exemplary embodiment of the present invention.

FIG. 4 to FIG. 6 show the safety scalpel 100 after assembly. FIG. 4 is a front, perspective view of the safety scalpel 100 with a blade in a retracted position within the shield 400. FIG. 5 is a front, perspective view of the safety scalpel 100 with the blade 600 in an extended position outside the shield 400. FIG. 6 is a rear, perspective view of the safety scalpel 100 with the blade 600 in a retracted position.

As shown in FIG. 1 and FIG. 7A to 7C, the handle 200 of the safety scalpel 100 includes a first end 202 and a second end 204. The handle 200 generally includes three portions which are:—a holding portion 210, a locking portion 220, and an engaging portion 230. The holding portion 210 extends from the first end 202 to the locking portion 220. The engaging portion 230 extends from the second end 204 to the locking portion 220.

The holding portion 210 of the handle 200 can include indicia. It may be desirable for the user of the safety scalpel 100 to make measurements or to calculate lengths while in use. Indicia, such as a scale 212, can be printed or etched on at least one side of the holding portion of the handle 200. In many embodiments, the scale 212 can be in inches, centimeters, millimeters, and the like.

The locking portion 220 of the handle 200 can engage an end of the cartridge assembly 300. As described in detail below, the locking portion 220 engages an end of the shield 400 and is keyed to mate with the shield 400 to reduce, if not eliminate, wobble of the cartridge assembly 300 relative to the handle 200.

The engaging portion 230 of the handle is adapted to be received in a hollow cavity of the cartridge assembly 300. The engaging portion 230 includes a rising ramp 232 along each of the opposing sides of the engaging portion 230, a defined cutout 234, a keyway 236 configured to receive a portion of the slider 500, a wobble prevention detent or bump 238, and an aperture 240 configured to receive a tab 410 from the shield 400 for locking the cartridge assembly 300 to the handle 200. The bump 238 engages with the slider 500 to prevent the blade 600 from wobbling when the safety scalpel 100 is operated in an operating position in a first direction whereas the keyway 236 of the handle 200 cooperates with an extending member 502 of the slider 500 (as shown in FIG. 11B) to prevent wobbling in a second direction.

Figure 8B:
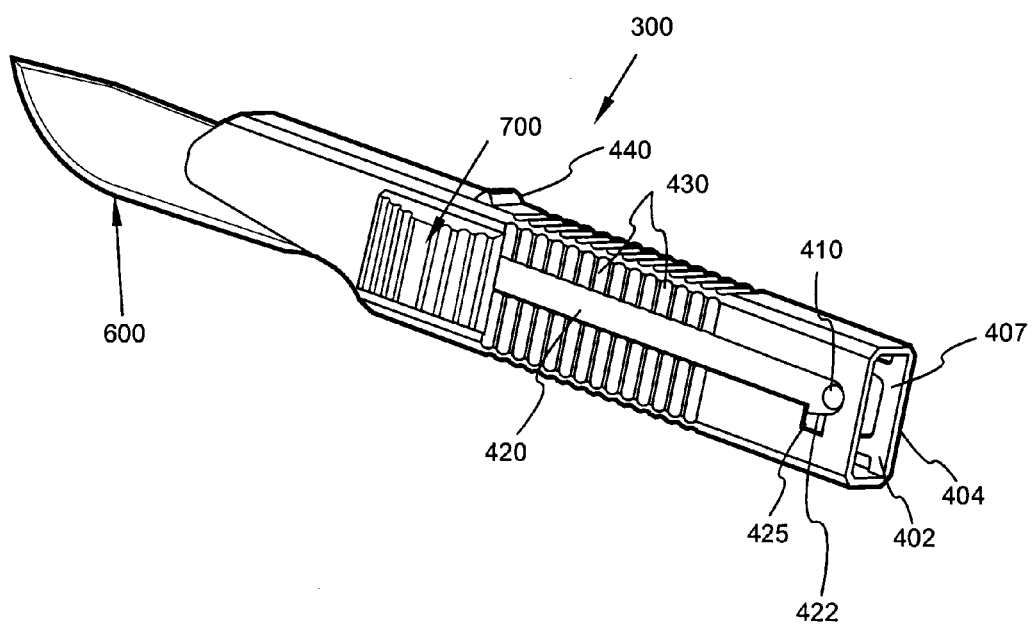
FIG. 8B is a front, perspective view of the cartridge assembly of the safety scalpel with an exposed blade, in accordance with an exemplary embodiment of the present invention.
Figure 9:
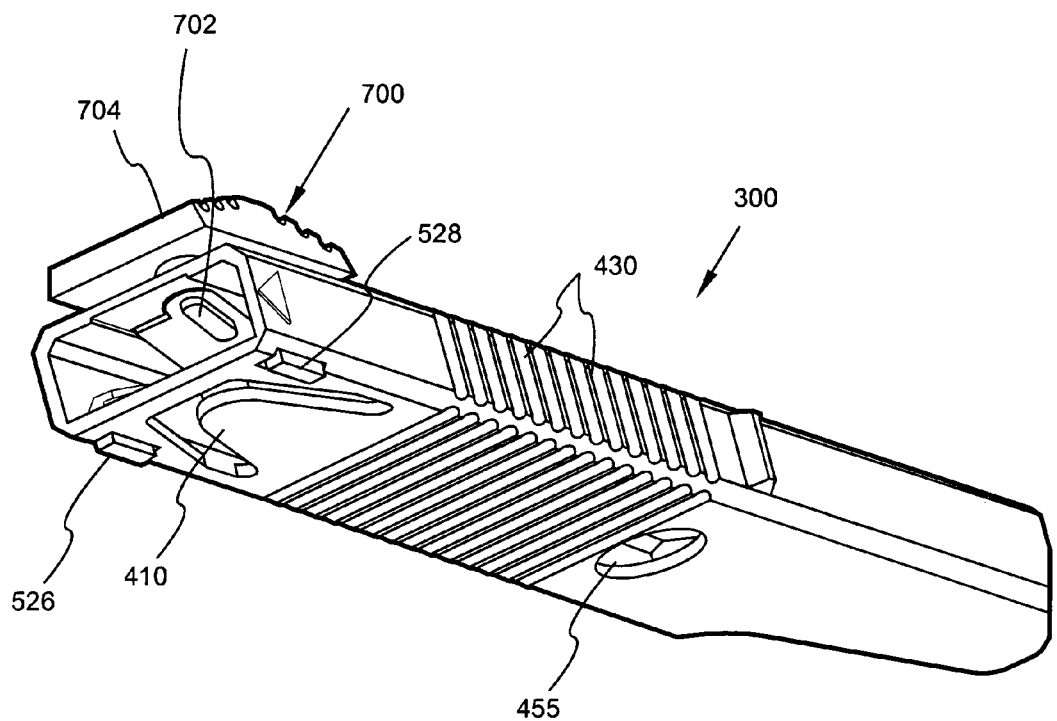
FIG. 9 is a rear, perspective view of the cartridge assembly of the safety scalpel, in accordance with an exemplary embodiment of the present invention.
Figure 10A:
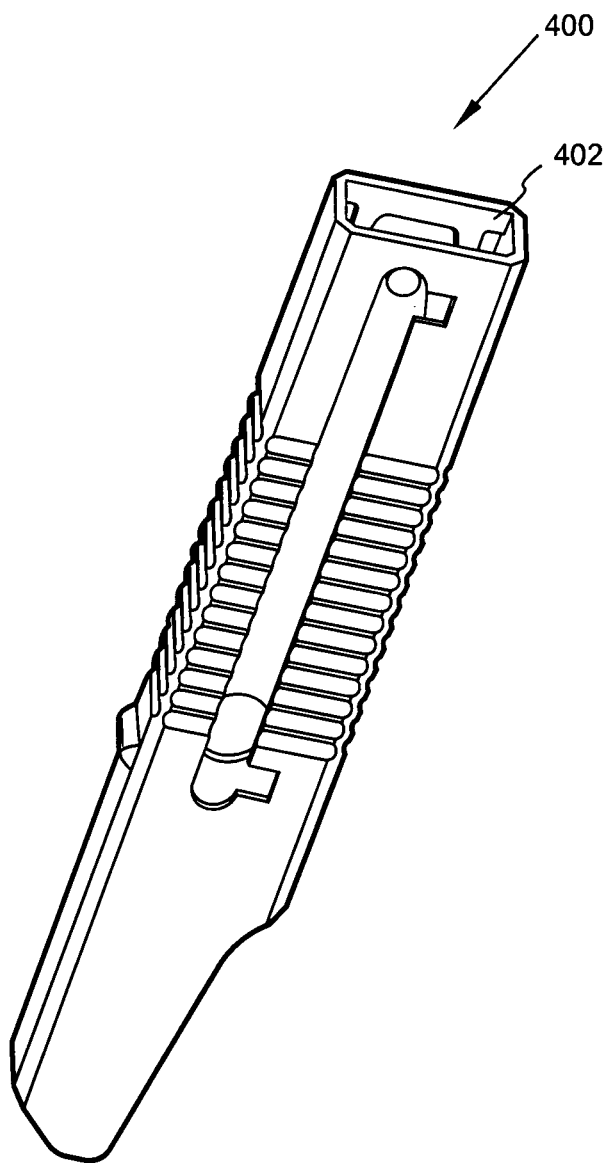
FIG. 10A is a front, perspective view of a shield of the cartridge assembly of the safety scalpel, in accordance with an exemplary embodiment of the present invention.
Figure 10B:
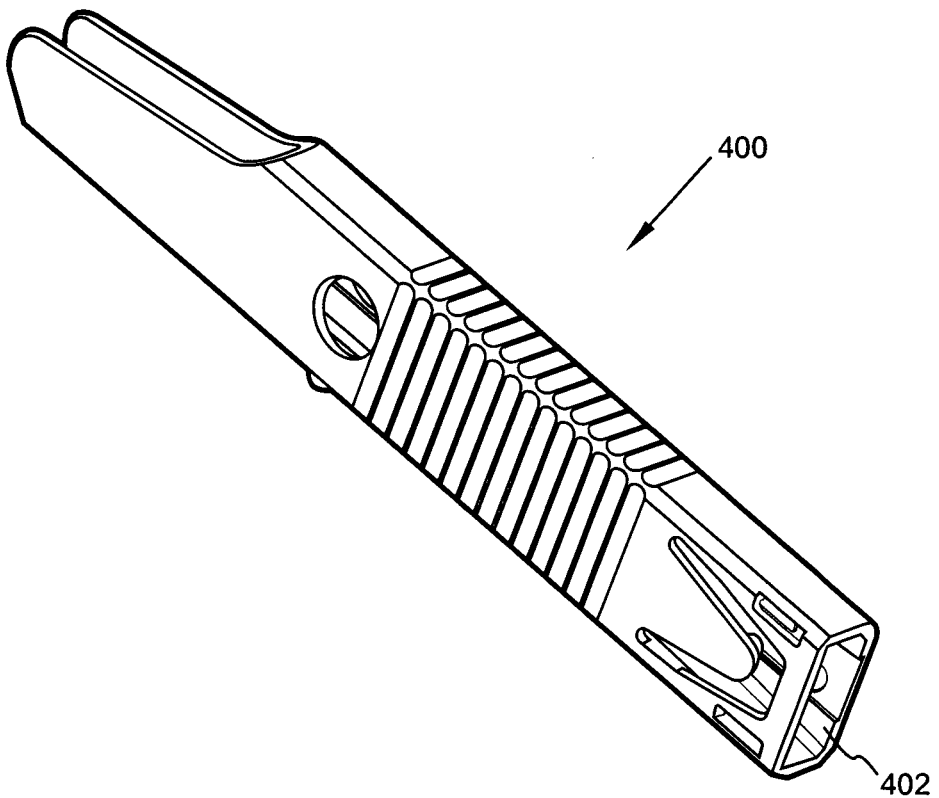
FIG. 10B is a rear perspective view of the shield of the cartridge assembly of the safety scalpel, in accordance with an exemplary embodiment of the present invention.
Figure 10C:
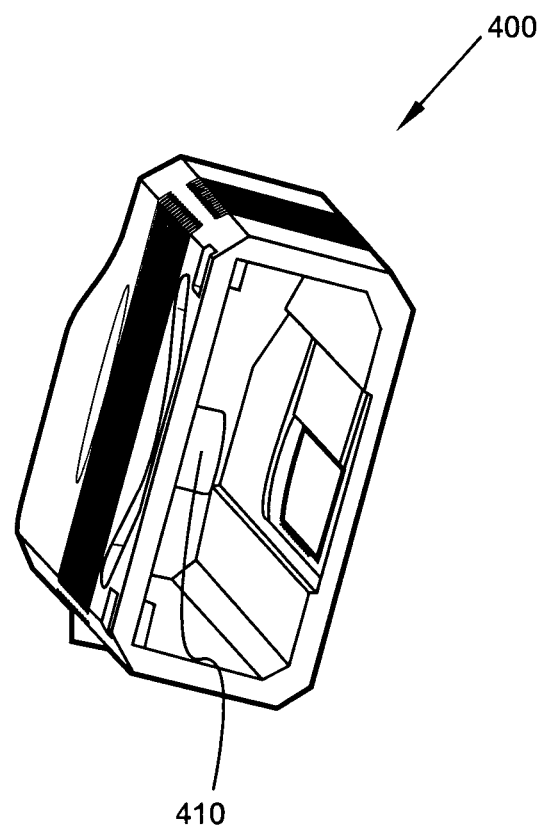
FIG. 10C is an end perspective view of the shield of the cartridge assembly of the safety scalpel, in accordance with an exemplary embodiment of the present invention.
Figure 10D:
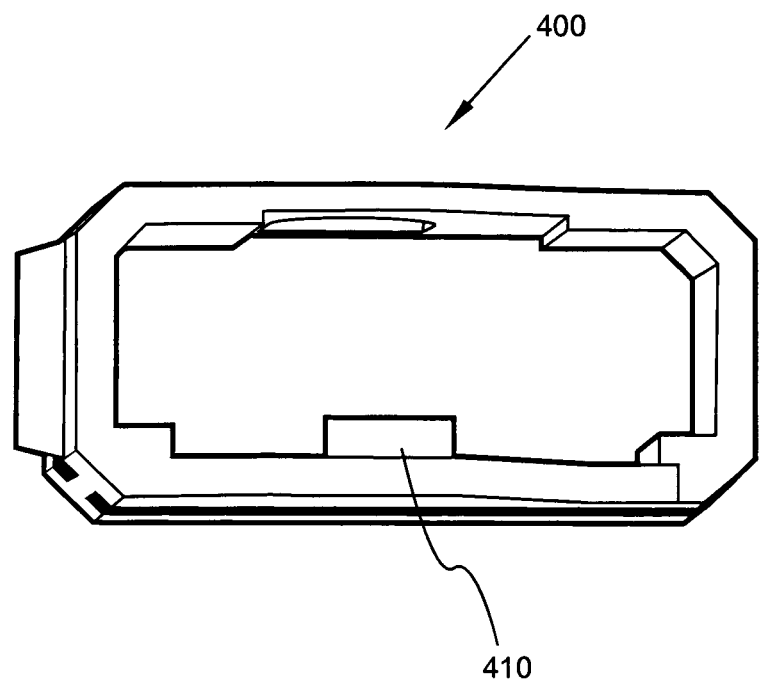
FIG. 10D is an end view into a hollow cavity of the shield of the cartridge assembly, in accordance with an exemplary embodiment of the present invention.

FIG. 8A is a front, perspective view of the cartridge assembly 300 with the blade 600 in a retracted position. FIG. 8B is a front, perspective view of the cartridge assembly with a blade in an extended position. As shown in FIGS. 8A and 8B, the cartridge assembly 300 has a shield or blade guard 400, a slider or blade holder 500 slideably mounted within a cavity 402 of the shield or blade guard 400, a blade 600, and a button 700 or an activation member 700. FIG. 9 is a rear, perspective view of the cartridge assembly 300, As shown in FIGS. 1-6 and 8A, 8B, 9, 10A to 10D, and 11, the shield 400 of the cartridge assembly 300 can be elongate, and having a substantially rectangular cross-section. Referring to FIG. 10A, the shield 400 can be substantially hollow, defining a cavity 402, and adapted to slide onto the second end 204, and cover up substantially the engaging portion 230, of the handle 200. The slider 500 can be disposed within the cavity 402 defined by the shield 400. In some embodiments, the slider 500 can slide along rails positioned within the cavity 402 of the shield 400.

The shield 400 extends from a first end 404, which is adapted to engage the locking portion 220 of the handle, to a second end 406. In an exemplary embodiment, the first end 404 is a handle engaging end, and the second end 406 is blade engaging end.

To prevent the cartridge assembly 300 from sliding off the handle 200 and/or moving relative to the handle 200 during use, the cartridge assembly 300 can be locked in position relative to the handle 300 once it is mounted onto the engaging portion 230 of the handle 200. The shield 400 of the cartridge assembly 300 can include a locking snap 410, which can be positioned on a second side of the shield 400. The locking snap or tab 410 engages the aperture 240 on the engaging portion of the handle 200 to prevent the cartridge assembly 300 from sliding off the handle 200 after it has been attached thereto. In other words, the aperture 240 can receive the locking snap 410.

Unlike many prior art solutions, in which removing the cartridge assembly 300 from the handle 200 may mistakenly occur, the safety scalpel 100 of the present invention prevents accidental removal of the cartridge assembly 300. In many embodiments, the cartridge assembly 300 can be disposable. When it is desired to dispose of the cartridge assembly 300, a worker removes the cartridge assembly 300 from the handle 200. To remove the cartridge assembly 300, the worker may need to implement forceps, pliers, or another like device. A nose of the device can lift the locking snap 410 of the shield 400 from the aperture 240 of the handle 200. Conventional designs enable the disassembly of the cartridge assembly 300 from the handle 200, but with dangerous consequences, including the potential of removal during use of the scalpel. The safety scalpel 100 prevents the accidental removal of the cartridge assembly 300 from the handle 200, as it requires the positive action of lifting the locking snap 410 from the aperture 240.

Referring back to the shield 400, it can have a slot 420 extending longitudinally along a first side. The slot 420 extends from a slider disengaged end 422, near the first end 404 of the shield 400, to a slider engaged end 424, near the second end 406. As described elsewhere, the slider 500 can further carry the button 700. The button 700 can be travel along the slot 420 from the first end (slider disengaged slot 422) to the second end (slider engaged end 424), and back. The button 700 can be attached to the slider 500 by a stem 702. A head 704 of the button 700 can be disposed outside of the shield 400 while the slider 500 remains within the shield 400.

At least one side of the shield 400 can include a grip 430. The grip 430 can comprise a plurality of u-shaped cutouts defined along the surface of a side of the shield 400. As illustrated in the figures, the grip 430 can be placed on more than one side/surface.

In addition, a position indicator or extending member 440 can extend from at least one side of the shield 400. When the safety scalpel 100 is being used, the position indicator 440 provides an immediate both visual and feel/touch indication of the location of the scalpel 100 by mimicking the transition step between handle and blade on a traditional scalpel that may be used to locate position or provide a tactile grip to prevent slippage. This can be helpful to determine how far the blade 600 is in the surface being cut, or generally to have a feel for where the blade is, and can provide mechanical leverage to prevent slippage during use. For example, the position indicator 440 provides an immediate indication of how far a surgeon has cut into the epidermis or tissue of a patient.

Figure 11A:
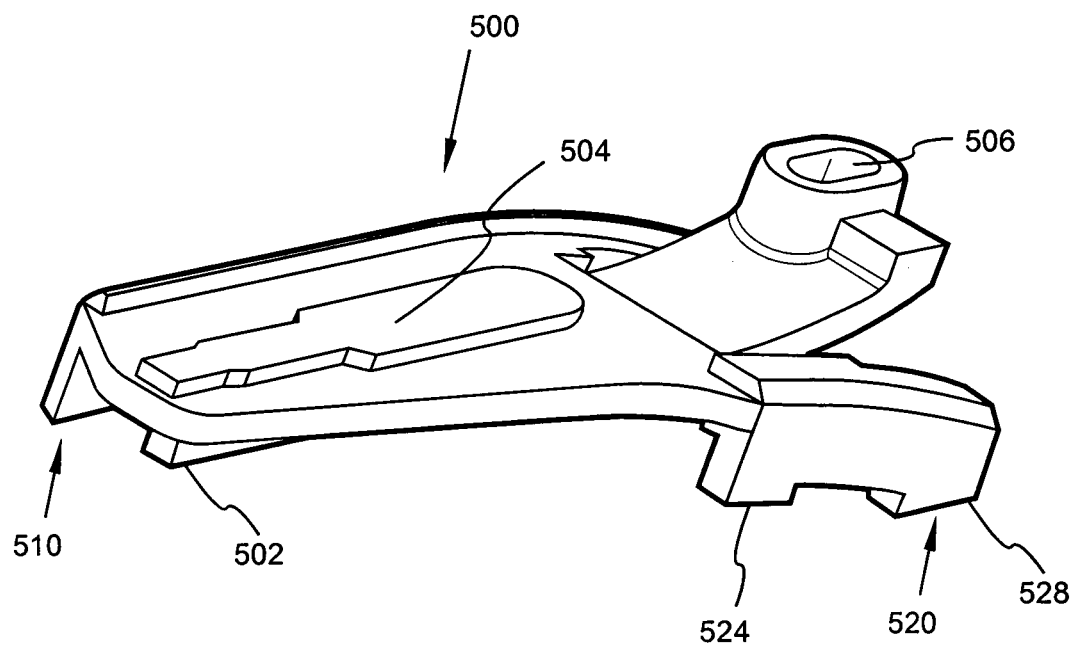
FIG. 11A is a top, perspective view of a slider of the cartridge assembly of the safety scalpel, in accordance with an exemplary embodiment of the present invention.
Figure 11B:
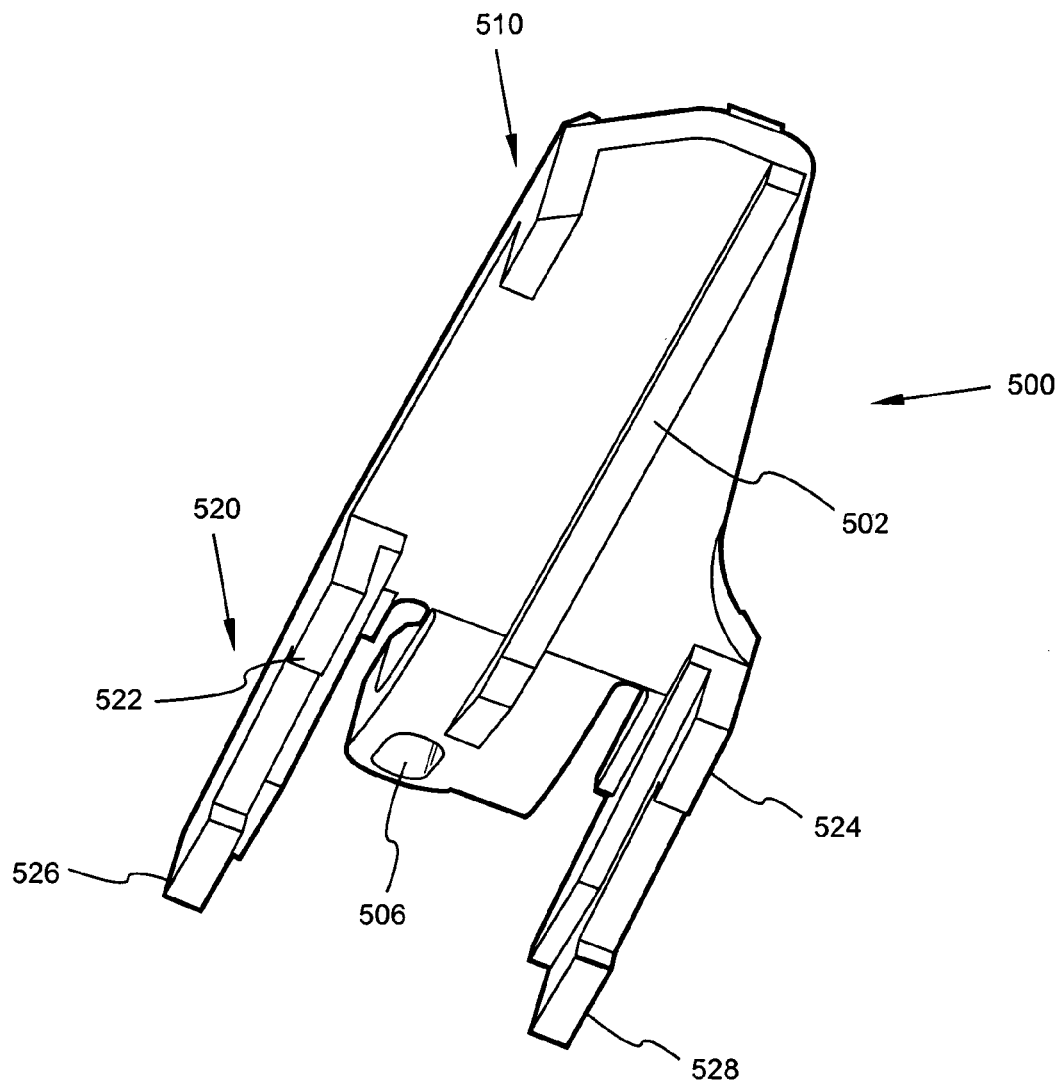
FIG. 11B is a bottom, perspective view of the slider of the cartridge assembly of the safety scalpel, in accordance with an exemplary embodiment of the present invention.

The slider 500, which is generally shown in FIGS. 1 and 11A to 11B, can slidably engage the handle 200 and shield 400. As the slider 500 slides relative to the shield 400 and handle 200, the slider 500 and the blade 600 can extend from within the shield 400 and retract back into the shield 400. A user, such as a surgeon or healthcare professional, can extend the blade 600 from within the shield 400 by moving the button 700 from the slider disengaged end 422 to the slider engaged end 424. The user can retract the blade 600 back into the shield 400 by moving the button 700 from the slider engaged end 424 back to the slider disengaged end 422.

The safety scalpel 100 can be stored with the blade 600 in the retracted position within the shield 400. In this position, the blade 600 is completely within the shield 400, wherein neither a point 602 nor a sharp, cutting edge 604 of the blade 600 is exposed.

Handling the scalpel 100 is safer with the blade 600 in the retracted position as accidental cuts can be avoided. In particular, the procedure of a nurse or scrub tech passing the scalpel 100 to a surgeon is made substantially safer as the edge of the blade 600 is not exposed and cannot cut either the surgeon or the nurse.

For increased safety, the slider 500 can be locked within the shield 400 to prevent the blade 600 from extending from within the housing 400 when the cartridge assembly 400 is not mounted on the handle 200.

FIGS. 1-2, 4-5, and 7A-7C illustrate perspective frontal views of an exemplary embodiment of a scalpel handle 200. The scalpel handle 200 can comprise a longitudinal axis 201, a holding portion 210 for gripping by the user, and an engaging portion 230 for receiving the blade cartridge 300. In an exemplary embodiment, the engaging portion 230 comprises approximately half the length of the scalpel handle 200 and the holding portion 210 comprises the remaining half. Between the holding portion 210 and the engaging portion 230 is the locking portion 220 that is sized and shaped to cooperatively fit within the first end 404 of the shield 400.

The engaging portion 230 of the handle 200 can be narrower and substantially thinner than the holding portion 210, so that it can fit within the cartridge assembly 300. Preferably, the engaging portion 230 can include a tapered tip 242 for improved insertion into the protective blade housing 400 and assembly of the safety scalpel 100.

A longitudinal groove or keyway 236 can be disposed along the engaging portion 230 of the handle 200 to accommodate and receive an extending member 502 of the slider 500 after mounting of the blade 600 to the slider 500 via a blade detent 504 and heat stakes.

The handle 200 can also include a wobble prevention detent 238, which is positioned in the engaging portion 230 of the handle. The wobble prevention detent 238, which in some embodiments is a bump or outwardly extending member, extends upwardly from the handle 200 and engages the slider 500 when the cartridge assembly 300 is positioned on the handle 200. The wobble prevention detent 238 can press on a bottom of the slider 500 and stabilize the blade 600 when the blade 600 extends from the cartridge assembly 300 and is in use.

For increased traction of the scalpel handle 200 when in contact with a finger during use of the safety scalpel 100, the handle portion 210 can include a plurality of grooves positioned on the front and/or back of the handle 200. The plurality of grooves can prevent slippage of the safety scalpel 100 during use.

As illustrated in the figures, the holding portion 210 of the scalpel handle 200 can include indicia 212. The indicia 212 can be generally located on the front face of the scalpel handle 200. The indicia 212 can include multiple markings or printings, the indicia 212 are preferably units of measurement such as, but not limited to, the metric system, the Imperial system, or many other appropriate measuring systems.

The handle 200 is designed to accept the cartridge assembly 300, and provide the user with the feel of a conventional scalpel when used. It is thus can be provided of materials, weight, and design for comfortable use by the user. In some embodiments, the handle 200 and the blade 600 can be made stainless steel, while the shield 400, the slider 500, and the button 700 are made of polycarbonate material(s).

FIGS. 1-6 and 8A-10D illustrates perspective views of the shield 400. The shield 400 can comprise a longitudinal axis, and can be elongate with a generally rectangular cross-section. The shield 400 is hollow, defining a cavity 402, having a first opening 407 at the first end 404 and a second opening 409 at the second end 406.

The shield 400 can comprise a slot 420 spanning the front side wall. The slot 420 can be elongate and oriented substantially parallel to the axis 201 of the scalpel 100. The slot 420 can comprise openings 422 and 424 at ends of the slot 420, i.e., the slider disengaging end 422 and slider engaging slot 424. The slots 422 and 424 can have an extension 425 for maintaining the slider in a set position.

The slider 500 can be inserted and housed within the shield 400. The stem 702 of the button 700 can be passed through the stem receiving aperture 506 of the slider 500 while the head 704 remains outside of the shield 400. The stem receiving aperture 506 is wide enough to accommodate the stem 702 of the button 700. A user can move the slider 500 within the shield 400 by first pushing down (towards the shield 500) and pushing or pulling on the button 700 in direction desired. As the slider 500 moves, the slot 420 prevents the slider 500 from moving in any direction except longitudinally parallel of the length of the shield 400 by limiting movement of the stem 702 of the button 700. The slot 420 also limits the total distance the slider 500 can travel because the stem 702 can only move within the confines of the slot 420. In some embodiments, the head 704 of the button 700 can have a plurality of ridges 705 on its surface to provide the user with a better grip when engaging the button 700.

As described, the safety scalpel 100 is configured to extend/retract the blade 600. For example, this familiar/intuitive action is similar to using a conventional box cutter device. As opposed to some of the conventional scalpels, where the user must slide the shield backwards to expose the blade and even more awkwardly slide the shield forward to consciously cover the blade, the present safety scalpel 100 is adapted to extend and retract the blade 600 by pushing downward on the button 700 and then sliding it laterally along the shield 400.

The shield 400 can be attached to the scalpel handle 200 by inserting the engaging portion 230 of the handle 200 through the first opening 407 of the shield 400. The shield 400 can slide along the engaging portion 230 until the end of the shield 400 abuts against the wall of the locking portion 220 of the handle 200, and the locking snap 410 engages the aperture 240.

The shield 400 can be detached from the handle by lifting the locking snap 410 from the aperture 240. This may require the use of a set of forceps, long nose pliers, or other similar tools. Once the locking snap 410 has been removed from the aperture 240, the shield 400, and more generally the cartridge assembly 300, can be removed by pulling the shield 300 in away from the holding portion 210 of the handle 200.

The slider engaging end 424 can facilitate locking the slider 500 in the extended position. This end secures the slider 500 in the extended position and prevents forces in the direction of the first end 404 generated by pressing the scalpel against an object from pushing the slider or blade holder 500 back into the protective blade housing 400. The slider 500 can be retracted by pressing the button 700 to disengage it from the slider engaging end 424, and pulling the button 700 in the direction of the first end 404.

For additional safety, the slider 500 can be locked within the shield 400 when the cartridge assembly 300 is not mounted to the handle to prevent accidental extension of the blade 600. As shown in FIG. 1, the shield 400 can comprise a slider locking aperture 450 located near the first end 404. The slider 500, on the other hand, includes a pair of legs—at least one front leg 510 and at least one rear leg 520. The rear leg 520 can include a front pair of feet 522 and 524 as well as a pair of back feet 526 and 528. The rear back feet 526 and 528, which can be spring loaded, are receivable in the locking aperture 450, which may comprise one or more holes. As illustrated in the figures, the locking aperture 450 can include two separate and distinct apertures, each of which receives at least one of the rear back feet 526 or 528. Because the rear back feet 526 and 528 of the shield 500 are locked within the locking aperture of the shield 400, the slider 500, which also carries the blade 600, cannot be moved to extend from the shield 400 and thus once assembled cannot accidentally cut or injure a user.

Figure 12:
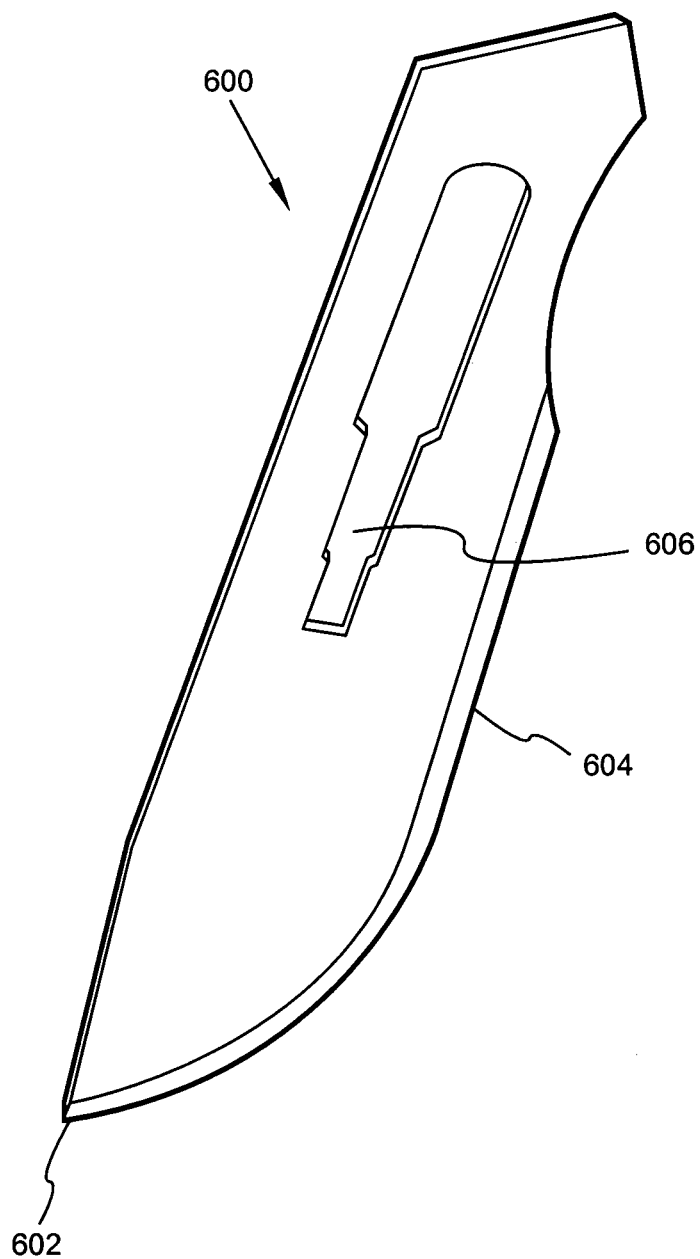
FIG. 12 is a perspective view of a blade of the cartridge assembly of the safety scalpel, in accordance with an exemplary embodiment of the present invention.

As mentioned, when the cartridge assembly 300 is fully assembled, the blade 600 cannot accidentally extend from the shield 400. A fully assembled cartridge assembly 300 includes the blade 600 carried by the slider 500. Referring to FIG. 12, the blade 600 has a blade point 602, a cutting edge 604, and a slider aperture 606. The extending member 504 of the slider 500 can engage and thus be received by the slider aperture 606 of the blade 600. The slider aperture 606 and the extending member 504 are keyed to cooperatively mate with one another. The slider 500 is then positionable within the cavity 402 of the shield 400. The slider 500 carrying the blade 600 can be inserted into the second opening 409 at the second end 406 of the shield 400.

Figure 13A:
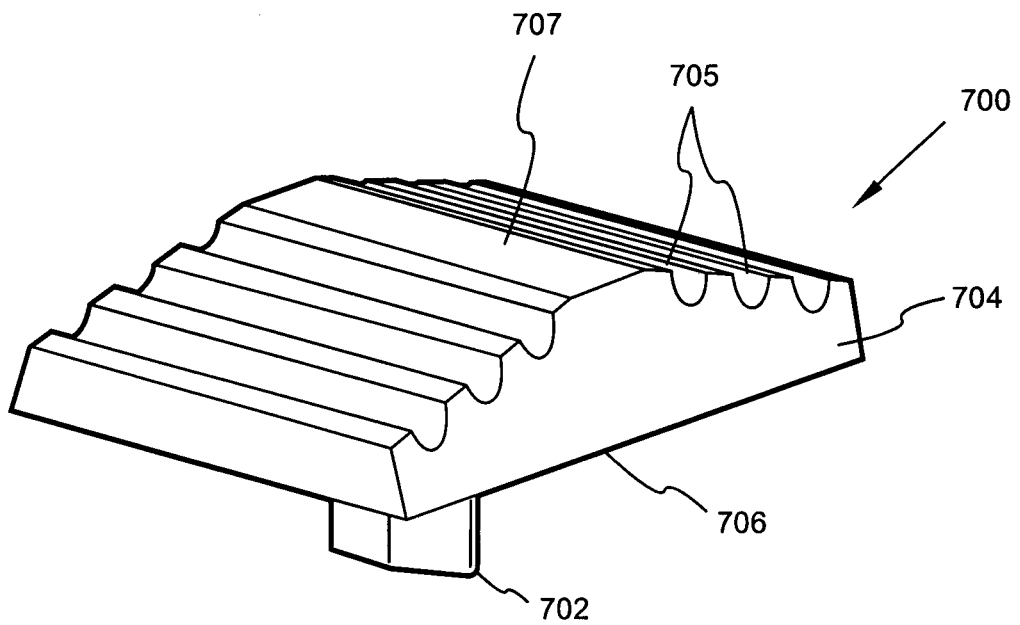
FIG. 13A is a top perspective view of a button of the cartridge assembly of the safety scalpel, in accordance with an exemplary embodiment of the present invention.
Figure 13B:
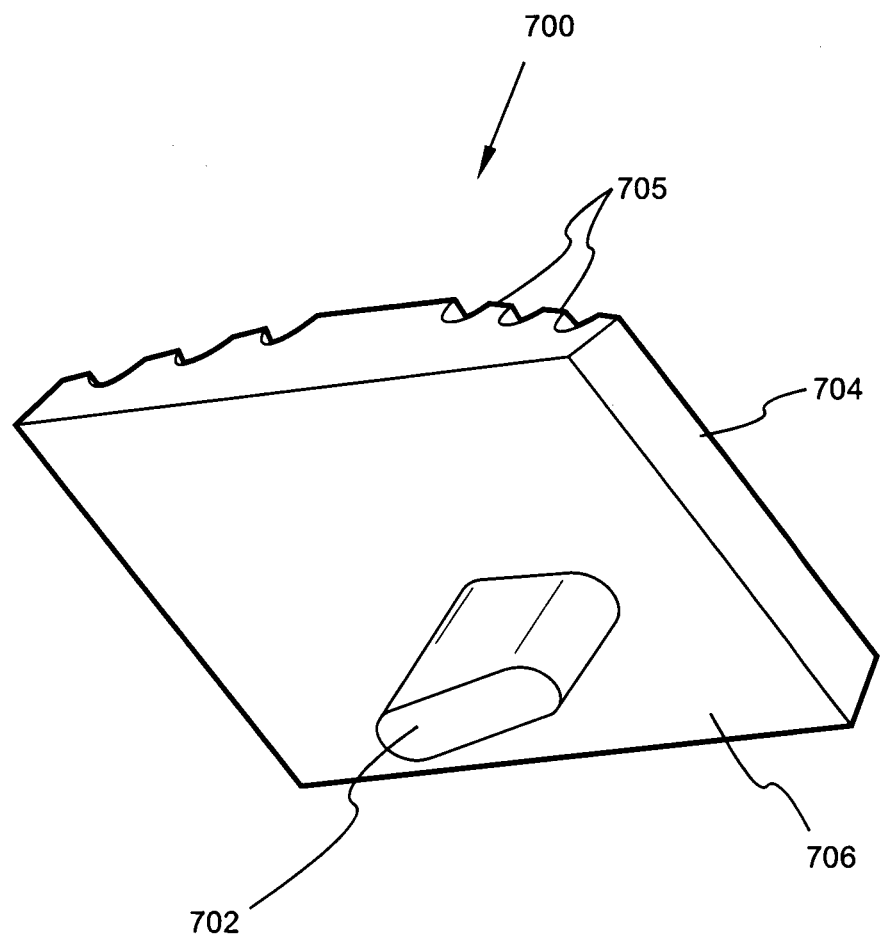
FIG. 13B is a bottom, perspective view of the button of the safety scalpel, in accordance with an exemplary embodiment of the present invention.

Now the button 700 can be connected to the slider 500. Referring to FIG. 13A and FIG. 13B, the button 700 has a head 704 have a first surface 706 and a second surface 707. The head 704 can have a stem 702 extending from the first surface 706. The head 704 can also comprise a plurality of ridges 705 on the second surface 707. The stem 702 can be inserted into the stem receiving aperture 506 of the slider 500. In some embodiments, it may be desirable to heat stake the stem 702 to the slider 500. In such embodiments, a heat stake hole 455 is positioned on the side of the shield 400 that opposes the slot 420. The required heat can be applied through the heat stake hole 455 to couple the stem 702 of the button to the slider 500. The button 700 can be slid along the slot 420, such that the slider 500 can be locked near the first end 404 of the shield 400. In this position, the rear feet 520 can be received in the locking aperture 450 of the shield 400. The slider 500 can be locked in the shield 400 by having its rear back feet 526 and 528 engage the aperture 450 of the shield 400. As a result, the slider 500 cannot be moved, unless placed on the handle 200, and the blade 600 does not extend from the shield 400.

When the cartridge assembly 300 is coupled to the handle 200, the slider 500 can be varied between an extending or engaging position, wherein the blade 600 can be used, or a disengaging or secured position, wherein the blade 600 is housed.

As mentioned above, the cartridge assembly 300 can be secured to the engaging portion 230 of the handle 200. The second end 204 of the handle 200 can be inserted into first opening 407 at the first end 404 of the shield 400. The handle 200 includes a pair of ramps 232 along opposing sides of the engaging portion 230. The extending member 502 of the slider 500 is sized to fit within the keyway 236 of the engaging portion 230. As the cartridge assembly 300 receives the engaging portion 230 of the handle 200, the extending member 502 engages the keyway 236 and the rear feet 520 slide along the ramp 232. When the cartridge assembly 300 is secured to the handle, which includes the locking snap 410 engaging the aperture 240, the first end 404 of the shield receives the locking portion 220 of the handle 200. The locking portion 220 is insertable into a portion of the first opening 407 of the first end 404 of the shield 400. For example, the first opening 407 can have chamfered corners to cooperatively engage the locking portion 220. As the cartridge assembly 300 slides along the engaging portion 230 of the handle, the rear feet 520 of the slider 500 slides along the ramp 236. This causes the rear feet 520 to lift up and out of the locking aperture 450 of the shield 400. Consequently, when the button 700 is depressed, the slider 500 can slide within the shield 400 and the button 700 can slide along the slot 420 of the shield 400 to ultimately expose and extend the blade 600.

When the button 700 is depressed, a portion of the bottom of the slider 500 can fall into the u-shaped cutout 234 of the engaging portion 230 of the handle. The cutout 234 is sized and shaped to receive the necessary portion of the slider 500 to enable the slider 500 to move along the engaging portion 230 of the handle 200.

The second opening 409 near second end of the shield 400 can be configured to allow the slider 500 to extend the blade 600 in direction outside of the shield 400 as the user moves the button 700 in the direction to extend the blade 600.

In some embodiments, the blade 600 can be heat staked to the slider 500. That is, the blade 600 can be secured to the slider 500 by applying heat, which locks the blade 600 securely in position.

Figure 14A:
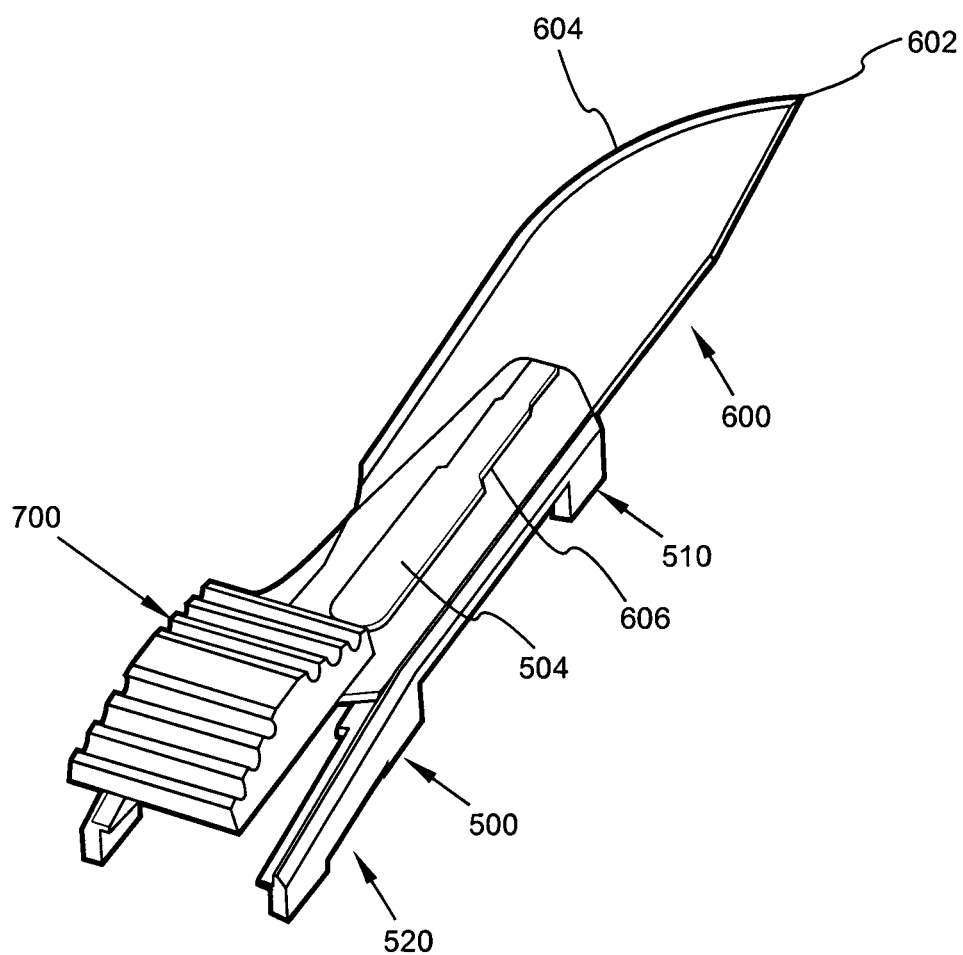
FIG. 14A is a top, perspective view of the slider of the cartridge assembly of the safety scalpel carrying a blade, in accordance with an exemplary embodiment of the present invention.
Figure 14B:
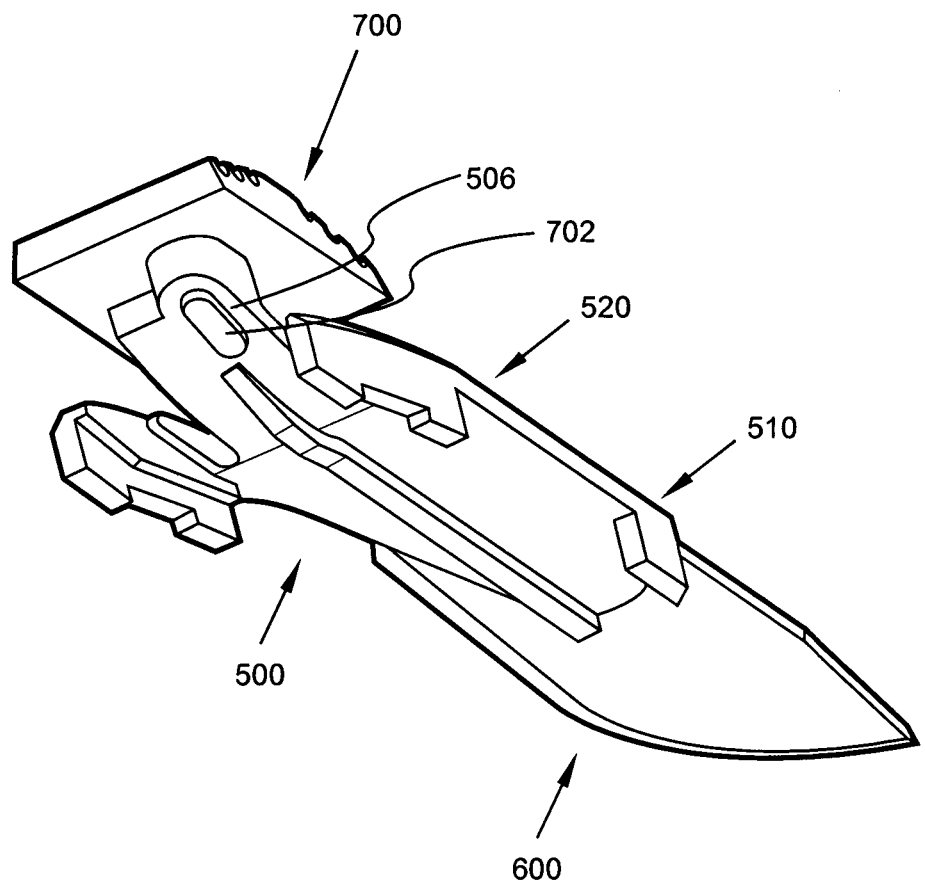
FIG. 14B is a bottom, perspective view of the slider of the cartridge assembly of the safety scalpel carrying the blade, in accordance with an exemplary embodiment of the present invention.

FIGS. 14A and 14B illustrate perspective views of an exemplary embodiment of a slider 500 with a blade 600 attached thereto. One skilled in the art will recognize that the blade 600 can be made of a variety of suitable materials including, but not limited to, both carbon and stainless steel. Generally, the carbon and stainless steel used to create the blade 600 are manufactured in compliance with several industry standards including British Standard ("BS") 2982:1992, International Organization for Standardization ("ISO") 7740:1985 and European Standard ("EN") 27740:1992. The blade 600 further can be sterilized by, for example, gamma radiation.

FIGS. 1-6 and 8A-9, 15A to 15B illustrate perspective views of exemplary embodiments of the cartridge assembly 300. As mentioned, the cartridge assembly 300 can comprise the shield 400, slider 500, and blade 600. The cartridge assembly 300 can be attached to the handle 200, and easily removed for disposal and/or replacement. The cartridge assembly 300 can be securely fitted onto the engaging portion 230 of the scalpel handle 200 by inserting the second end 204 through the first opening 407. The locking snap 410 can engage the aperture 240 to secure the cartridge assembly 300 onto the handle 200, preventing the cartridge 300 from sliding off the handle 200 during use.

The slider 500 can be disposed within the shield 400, between the engaging portion 230 of the scalpel handle 200 and a front side wall of the shield 400. The slider 500 can slide over the engaging portion 230 as a user moves the button 700.

The slider 500 can be retracted from the locked position by depressing and pulling the button 700 towards the second end 406 of the shield 400. The scalpel 100 is designed to be stored and handled with the slider 500 fully retracted. In this position, the blade 600 is fully enveloped by the shield 400, and the scalpel 100 is safe to handle because the sharp edge of the blade 600 is not exposed.

The cartridge assembly 300 can be removed from the handle 200, when the slider 500 is in the retracted position. This involves removing the locking snap 410 from the aperture 240.

Figure 15A:
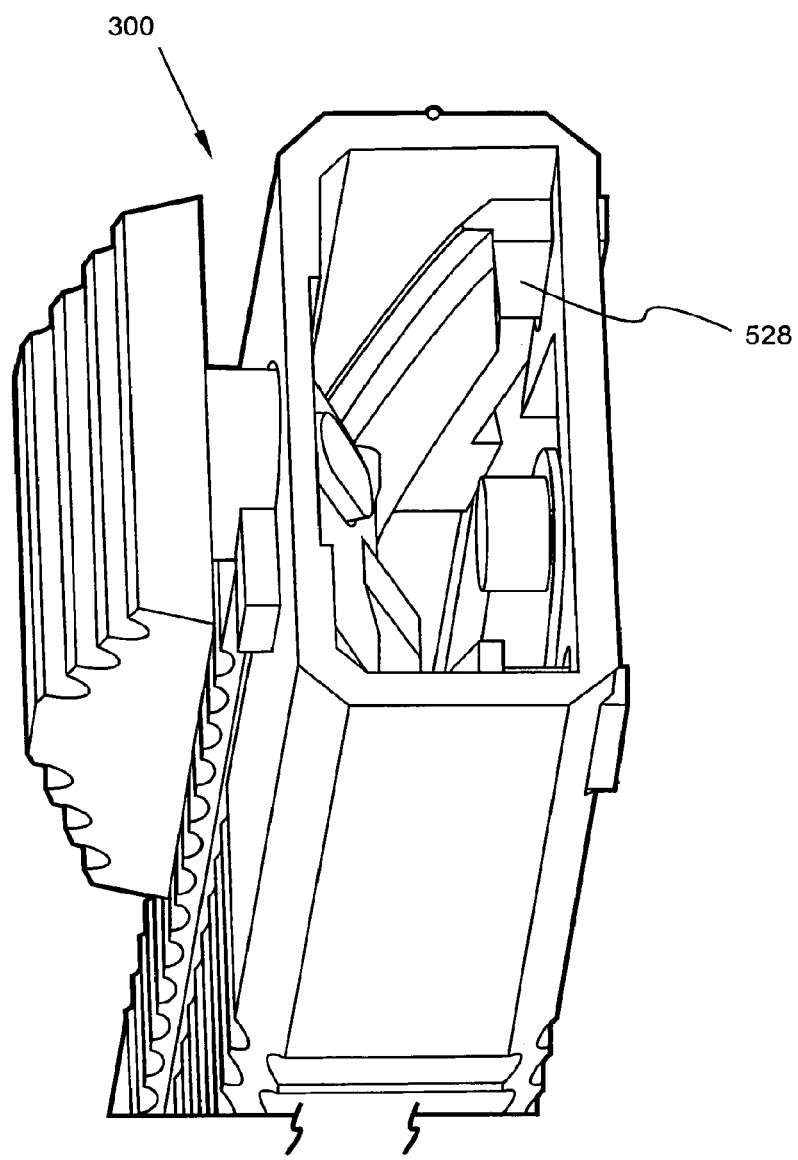
FIG. 15A is a perspective view of a cartridge assembly in accordance with an exemplary embodiment of the present invention.
Figure 15B:
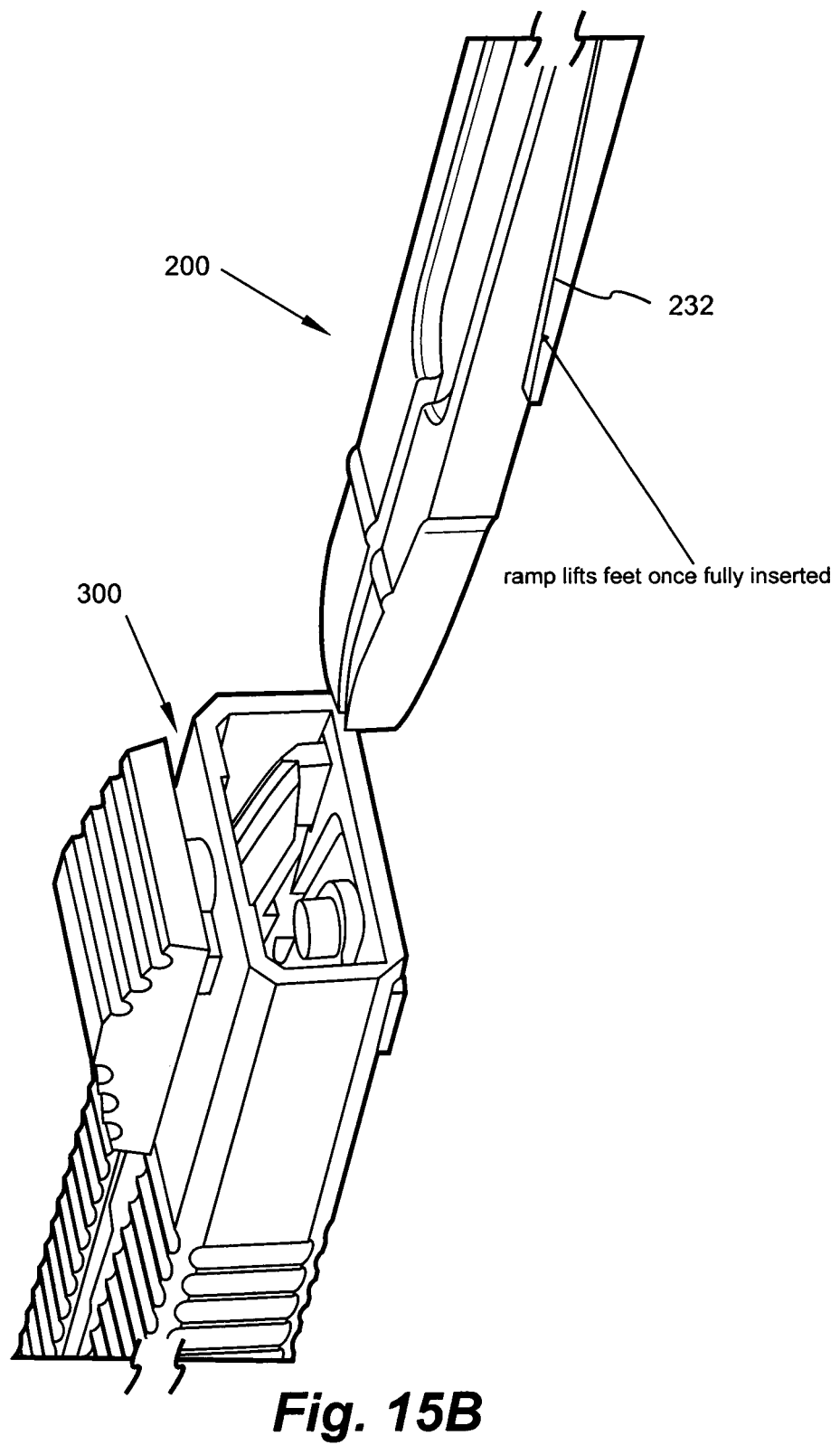
FIG. 15B is a perspective view of the cartridge assembly before insertion of a handle to form a safety scalpel in accordance with an exemplary embodiment of the present invention.

FIG. 15A is a perspective view of the cartridge assembly 300 before insertion of the handle 200. In particular, the spring loaded rear back feet 526, 528 is configured to prevent extension of the blade 600 without insertion of the handle 200. Specifically the back feet 526, 528 are locked within the slider locking apertures 450 located near the first end 404 of the shield. In this way, the slider 500 with the blade 600 is locked within the shield 400 to prevent the blade 600 from accidentally extending out of the shield without mounting the handle. To unlock the slider, as shown in FIG. 15B, the back feet 526, 528 can be lifted or raised out of from the apertures 450 by inserting the handle 200. Specifically, by inserting the handle 200, each of the ramps 232 lifts the respective feet 526, 528. Once the handle 200 is inserted into the cartridge assembly 300, a locking snap 410 of the shield 400 engages the aperture 240 on the engaging portion of the handle 200 to prevent the cartridge assembly 300 from sliding off the handle 200 after it has been attached thereto. In other words, the aperture 240 can receive the locking snap 410. The cartridge assembly 300 can be detached from the handle 200 by two hands and an external instrument, for example, by using the external instrument to lift the locking snap 410 from the aperture 240. For example, the locking snap 410 can be lifted from the aperture 240 by an unlock tool suitable for unlocking a snap lock or a locking snap so as to detach the cartridge assembly 300 from the handle 200. The unlock tool may be tweezers. The advantage of only using an external instrument to detach the cartridge assembly 300 is to prevent accidental detachment of the cartridge assembly 300 from the handle 200 during an inadvertent hand action when in an operating position or during handling of the safety scalpel 100. By requiring two hands to detach the cartridge assembly 300, i.e. one hand to hold the scalpel 100 and another hand to use an external instrument to lift the locking snap 410 from the aperture 240, the risks of accidental detachment of cartridge assembly 300 can be reduced.

In addition, in all the above embodiments, the handle 200, and in particular, the surfaces for gripping such as the holding portion 210 of the handle 200, can be made of or coated with a anti-slip material such as rubber material that can improve the friction between the hand and the grip surfaces. For example, the holding portion 210 may be coated with a synthetic rubber material. The handle 200 can be made of a metal material. The blade guard, the blade holder, and the activation member can be made of materials not limited to plastics, such as a thermoplastic material such as for example, polycarbonate materials.

From the foregoing, it can be seen that the invention provides a number of cutting devices. The various embodiments of the invention described above provide a safety scalpel having a handle for holding a cutting portion and a disposable cartridge assembly.

Embodiments of the present invention can be embodied in other specific forms without departing from the spirit or essential characteristics thereof. For example, while embodiments of the invention have been described in the context of a safety scalpel for use by a surgeon the concepts described herein need not be limited to these illustrative embodiments.

Whereas the above embodiments have been described in detail with accompanying figures, it will be understood that various changes from these embodiments can be made without departing from the scope of the invention.

What is claimed is:
1. A safety scalpel, comprising:
a handle having a first end and a second end and having a longitudinal axis that extends between the first end and the second end, comprising:
a holding portion extending from the first end to a locking portion, the locking portion positioned between the first end and the second end; and
an engaging portion extending from the second end to the locking portion; and a cartridge assembly detachably and slideably mounted onto the engaging portion of the handle substantially parallel to the longitudinal axis, comprising:
- a blade guard having a first end and a second end and a locking aperture defined near the first end, the blade guard defining a substantially cavity, wherein the blade guard slideably mounts onto the second end of the handle such that it covers the engaging portion and the first end of the blade guard engages the locking portion;
- a blade holder slideably mounted within the cavity of the blade guard, the blade holder having at least one front leg and at least one rear leg, wherein the at least one rear leg has a pair of front feet and a pair of back feet, the pair of back feet being spring loadable and receivable within the locking aperture of the blade guard;
- a blade keyed to cooperatively mate with the blade holder, such that as the blade holder slides within the cavity of the blade guard, the blade extends from or retracts within the second end of the blade guard; and
- an activation member attached to the blade holder, wherein the activation member is adapted for actuating the blade holder to move a portion of the blade between an extended position outside the second end of the blade guard and a retracted position within the second end of the blade guard.

2. The safety scalpel of claim 1, the activation member comprising a stem that is insertable into a stem receiving aperture of the blade holder.

3. The safety scalpel of claim 1, the engaging portion of the handle having a wall limiting how far the cartridge assembly slideably mounts onto the handle.

4. The safety scalpel of claim 1, the holding portion of the handle including indicia.

5. The safety scalpel of claim 1, wherein the locking portion engages the first end of the blade guard and is keyed to mate with the blade guard to substantially reduce wobble of the cartridge assembly relative to the handle.

6. The safety scalpel of claim 1, wherein the handle includes a wobble prevention detent extending from the handle for engaging the blade holder to substantially reduce wobble of the blade relative to the handle in the extended position.

7. The safety scalpel of claim 1, wherein the cartridge assembly comprises a locking snap positioned on a side of the blade guard, wherein the locking snap engages an aperture on the engaging portion of the handle to prevent the cartridge assembly from sliding off the handle after it has been attached thereto.

8. The safety scalpel of claim 7, wherein the cartridge assembly is detached from the handle by lifting the locking snap from the aperture.

9. The safety scalpel of claim 1, wherein at least one side of the blade guard includes a grip, wherein the grip comprises a plurality of u-shaped cutouts defined along a surface of the at least one side of the blade guard.

10. The safety scalpel of claim 1, further comprising a position indicator that extends from at least one side of the blade guard, the position indicator providing a visual and touch indication of how far a user has cut into the tissue of a patient.

11. The safety scalpel of claim 1, wherein the engaging portion of the handle is narrower and substantially thinner than the holding portion of the handle to accommodate the cartridge assembly.

12. The safety scalpel of claim 1, wherein the handle is stainless steel.

13. The safety scalpel of claim 1, wherein the blade is carbon, stainless steel, or combinations thereof.

14. The safety scalpel of claim 1, wherein the blade guard, the blade holder, and the activation member are made of polycarbonate materials.

15. The safety scalpel of claim 1, wherein the cartridge assembly is disposable.

16. The safety scalpel of claim 1, the handle further comprising a pair of ramps along opposing sides of the engaging portion, wherein the at least one rear leg of the blade holder slides along and onto the pair of ramps.

17. A safety scalpel, comprising:
- a handle having a first end and a second end and having a longitudinal axis that extends between the first end and the second end, and
- a cartridge assembly detachably and slideably mounted onto at least a portion of the handle along the longitudinal axis, comprising:
  - a blade guard having a first end and a second end and a locking aperture defined near the first end, the blade guard defining a substantially hollow cavity, wherein the blade guard slideably mounts onto the second end of the handle;
  - a blade holder slideably mounted within the cavity of the blade guard, the blade holder having at least one front leg and at least one rear leg, wherein the at least one rear leg has a pair of front feet and a pair of back feet, the pair of back feet being spring loadable and receivable within the locking aperture of the blade guard;
  - a blade keyed to cooperatively mate with the blade holder, such that as the blade holder slides within the cavity of the blade guard, the blade extends from or retracts within the second end of the blade guard.

18. The safety scalpel of claim 17, wherein the cartridge assembly further comprises an activation member attached to the blade holder, wherein the activation member actuates the blade holder to extend and retract the blade.

19. The safety scalpel of claim 18, the activation member comprising a stem that is insertable into a stem receiving aperture of the blade holder 20. The safety scalpel of claim 17, wherein the cartridge assembly comprises a locking snap positioned on a side of the blade guard, wherein the locking snap engages an aperture on the handle to prevent the cartridge assembly from sliding off the handle after is has been attached thereto.

21. The safety scalpel of claim 17, wherein at least one side of the blade guard includes a grip, wherein the grip comprises a plurality of u-shaped cutouts defined along a surface of the at least one side of the blade guard.

22. The safety scalpel of claim 17, further comprising a position indicator that extends from at least one side of the blade guard, the position indicator providing a visual and touch indication of how far a user has cut into the tissue of a patient.

23. The safety scalpel of claim 17, wherein the handle is stainless steel.

24. The safety scalpel of claim 17, wherein the blade is carbon, stainless steel, or combinations thereof.

25. The safety scalpel of claim 16, wherein the blade guard, the blade holder, and the activation member are made of polycarbonate materials.

26. The safety scalpel of claim 16, wherein the cartridge assembly is disposable.

* * * * *

UNITED STATES PATENT AND TRADEMARK OFFICE
CERTIFICATE OF CORRECTION

PATENT NO. : 8,567,072 B2
APPLICATION NO. : 13/701510
DATED : October 29, 2013
INVENTOR(S) : Patrick Yi and George Hatzilias It is certified that error appears in the above-identified patent and that said Letters Patent is hereby corrected as shown below:

In the claims, Column 14 Line 63, Claim 26, "The safety scalpel of Claim 16" should read "The safety scalpel of Claim 17".

Signed and Sealed this
Eleventh Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,567,072 B2
APPLICATION NO. : 13/701510
DATED : October 29, 2013
INVENTOR(S) : Patrick Yi and George Hatzilias Page 1 of 1

It is certified that error appears in the above-identified patent and that said Letters Patent is hereby corrected as shown below:

In the Claims

Column 14 line 60, claim 25, "The safety scalpel of Claim 16" should read "The safety scalpel of Claim 18".

Signed and Sealed this
Fifteenth Day of April, 2014

Michelle K. Lee
*Deputy Director of the United States Patent and Trademark Office*